(12) United States Patent
Ramesh et al.

(10) Patent No.: US 10,716,938 B2
(45) Date of Patent: Jul. 21, 2020

(54) LEAD ENGAGEMENT DEVICES AND METHODS FOR ELECTRICAL STIMULATION AND/OR MONITORING SYSTEMS

(71) Applicant: LivaNova USA, Inc., Houston, TX (US)

(72) Inventors: Rajesh Ramesh, Houston, TX (US); David L. Thompson, Houston, TX (US); Steven W. Allis, Friendswood, TX (US)

(73) Assignee: LivaNova USA, Inc., Houston, TX (US)

( * ) Notice: Subject to any disclaimer, the term of this patent is extended or adjusted under 35 U.S.C. 154(b) by 154 days.

(21) Appl. No.: 15/920,247

(22) Filed: Mar. 13, 2018

(65) Prior Publication Data

US 2018/0200511 A1    Jul. 19, 2018

Related U.S. Application Data

(63) Continuation of application No. 14/694,848, filed on Apr. 23, 2015, now Pat. No. 9,943,685.

(51) Int. Cl.
*A61N 1/36* (2006.01)
*A61N 1/375* (2006.01)

(52) U.S. Cl.
CPC ............ *A61N 1/36* (2013.01); *A61N 1/3752* (2013.01)

(58) Field of Classification Search
CPC ................................ A61N 1/36; A61N 1/3752
See application file for complete search history.

(56) References Cited

U.S. PATENT DOCUMENTS

| 845,265 A | 2/1907 | Schade, Jr. |
| 845,268 A | 2/1907 | Schade |

(Continued)

FOREIGN PATENT DOCUMENTS

| EP | 0 890 371 | 1/1999 |
| EP | 0 900 577 | 3/1999 |
| FR | 2662310 | 11/1991 |

OTHER PUBLICATIONS

International Search Report and Written Opinion for Patent Application No. PCT/US2016/028491, dated Jul. 22, 2016, 11 pages.

*Primary Examiner* — George Manuel
(74) *Attorney, Agent, or Firm* — Foley & Lardner LLP

(57) ABSTRACT

According to aspects of the present disclosure, an implantable pulse generator includes a housing, a header, and a retainer device. The housing includes circuitry and a battery. The header is coupled to the housing and includes a bore configured to receive an end of a lead, and a passage disposed transverse to the bore and extending between an exterior surface of the header and an anchor cavity that extends into the header from the bore. The header supports at least one electrical contact within the bore coupled to the circuitry. The retainer device includes a looped member arranged within the bore, a proximal end extending at least partially into the passage, and anchored at a distal end by the anchor cavity. The looped member has a first position defining a first loop diameter that permits egress of the lead into the bore and a second position defining a second loop diameter that occludes at least a portion of the bore and is configured to engage at least two opposing sides of the lead sufficiently to prevent egress of the lead from the bore. The first loop diameter is greater than the second loop diameter.

20 Claims, 21 Drawing Sheets

(56) References Cited

U.S. PATENT DOCUMENTS

| | | |
|---|---|---|
| 1,005,283 A | 10/1911 | Neher |
| 1,363,350 A | 12/1920 | Recker |
| 1,661,124 A | 2/1928 | Koretzky |
| 2,027,220 A | 1/1936 | Benson |
| 2,222,715 A | 11/1940 | Kuhlman |
| 2,528,121 A | 10/1950 | Dickinson |
| 3,477,060 A | 11/1969 | Lawlor |
| 3,596,229 A | 7/1971 | Hohorst |
| 3,984,655 A | 10/1976 | Wahl |
| 4,245,642 A | 1/1981 | Skubitz et al. |
| 4,311,359 A | 1/1982 | Keller |
| 4,347,849 A | 9/1982 | Congdon |
| 4,410,228 A | 10/1983 | Stephenson |
| 4,540,236 A | 9/1985 | Peers-Trevarton |
| 4,708,417 A | 11/1987 | Woertz |
| 4,848,346 A | 7/1989 | Crawford |
| 5,012,807 A * | 5/1991 | Stutz, Jr. ............. A61N 1/3752 607/37 |
| 5,252,090 A | 10/1993 | Giurtino et al. |
| 5,275,620 A | 1/1994 | Darby et al. |
| 5,421,749 A | 6/1995 | Schrauder |
| 5,885,116 A | 3/1999 | Byfield, Jr. |
| 5,919,065 A | 7/1999 | Warner et al. |
| 5,993,244 A | 11/1999 | Bechaz et al. |
| 6,112,120 A | 8/2000 | Correas |
| 6,134,917 A | 10/2000 | Kohl et al. |
| 6,154,678 A | 11/2000 | Lauro |
| 6,196,883 B1 | 3/2001 | Bechaz et al. |
| 6,264,498 B1 | 7/2001 | Froberg |
| 6,312,297 B1 | 11/2001 | Lorkowski |
| 6,487,430 B1 | 11/2002 | Henderson et al. |
| 6,783,385 B2 | 8/2004 | Rudy |
| 6,859,667 B2 | 2/2005 | Goode |
| 6,895,276 B2 | 5/2005 | Kast et al. |
| 6,975,906 B2 | 12/2005 | Rusin et al. |
| 7,069,081 B2 | 6/2006 | Biggs et al. |
| 7,110,819 B1 | 9/2006 | O'Hara |
| 7,155,283 B2 | 12/2006 | Ries et al. |
| 7,167,749 B2 | 1/2007 | Biggs et al. |
| 7,174,219 B2 | 2/2007 | Wahlstrand et al. |
| 7,212,869 B2 | 5/2007 | Wahlstrom et al. |
| 7,225,025 B2 | 5/2007 | Goode |
| 7,234,981 B2 | 6/2007 | Eppe et al. |
| 7,274,963 B2 | 9/2007 | Spadgenske |
| 7,299,095 B1 | 11/2007 | Barlow et al. |
| 7,570,998 B2 | 8/2009 | Zhang et al. |
| 7,607,953 B2 | 10/2009 | Fabian |
| 7,630,768 B1 | 12/2009 | Coffed et al. |
| 7,650,191 B1 | 1/2010 | Lim et al. |
| 7,751,893 B2 | 7/2010 | Biggs et al. |
| 7,892,017 B2 | 2/2011 | Meyer et al. |
| 7,903,043 B2 | 3/2011 | Rawat et al. |
| 8,103,348 B1 | 1/2012 | Coffed et al. |
| 8,233,986 B2 | 7/2012 | Deininger et al. |
| 8,290,592 B2 | 10/2012 | Kane et al. |
| 8,346,362 B2 | 1/2013 | Kinney et al. |
| 8,543,209 B2 | 9/2013 | Tyers et al. |
| 8,577,453 B1 | 11/2013 | Stevenson et al. |
| 8,619,002 B2 | 12/2013 | Rawat et al. |
| 8,649,869 B2 | 2/2014 | Imani et al. |
| 8,727,817 B2 | 5/2014 | D'Hiver et al. |
| 8,989,872 B2 | 3/2015 | Prasannakumar et al. |
| 2005/0222642 A1 | 10/2005 | Przybyszewski et al. |
| 2005/0272280 A1 | 12/2005 | Osypka |
| 2006/0089681 A1 | 4/2006 | Tumlinson et al. |
| 2007/0060991 A1 | 3/2007 | North et al. |
| 2008/0200925 A1 | 8/2008 | Johnson et al. |
| 2010/0267265 A1 | 10/2010 | Dilmaghanian |
| 2012/0185019 A1 | 7/2012 | Schramm et al. |

\* cited by examiner

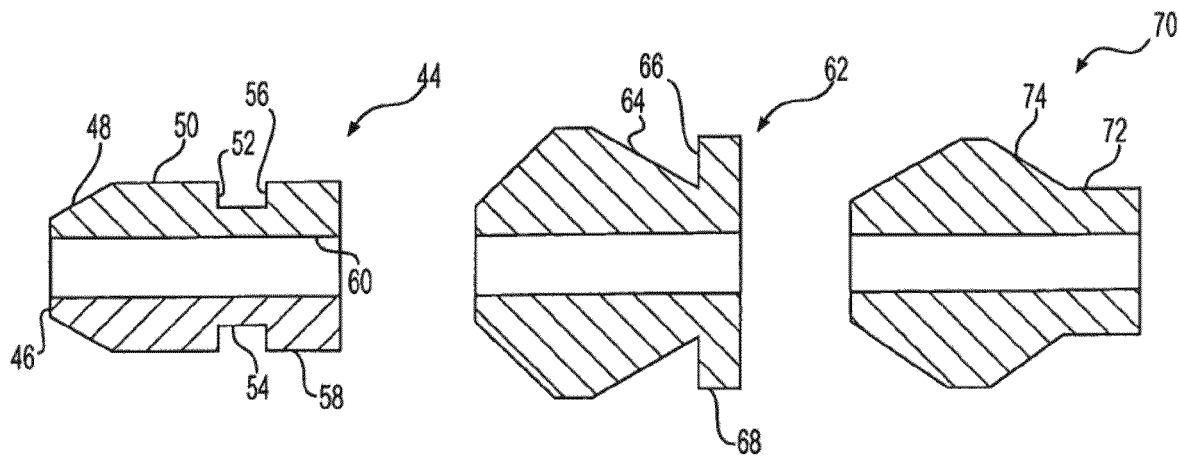
FIG. 4A   FIG. 4B   FIG. 4C
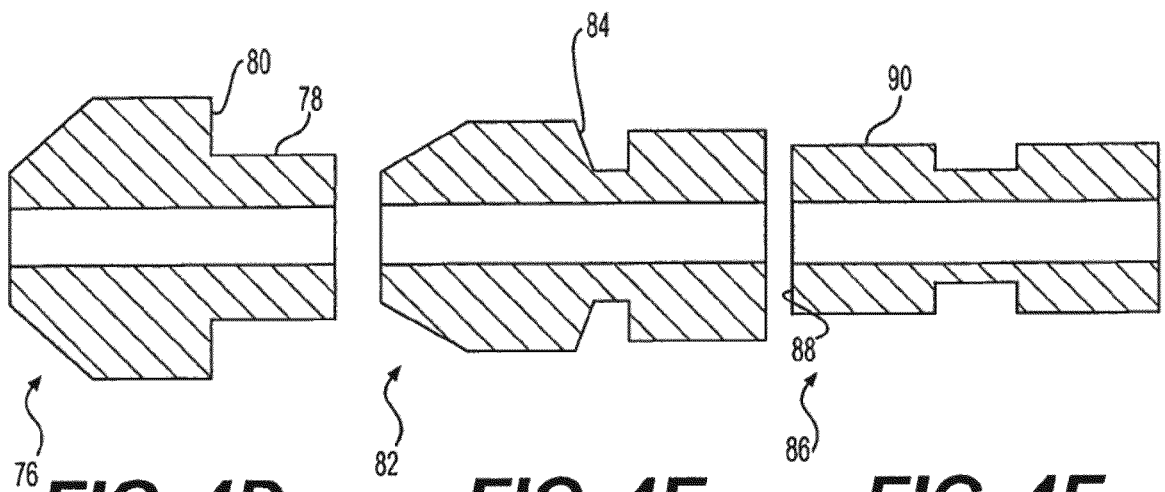
FIG. 4D   FIG. 4E   FIG. 4F
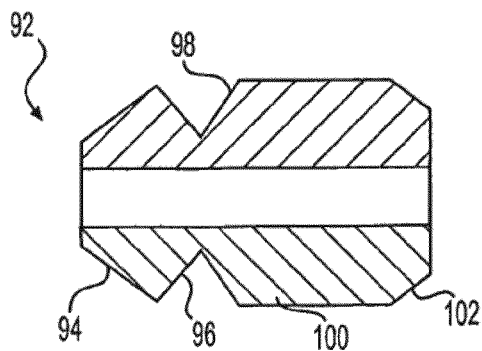
FIG. 4G
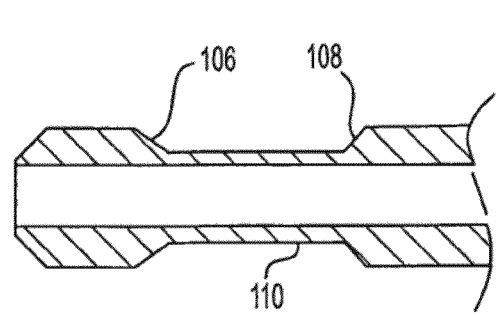
FIG. 4H

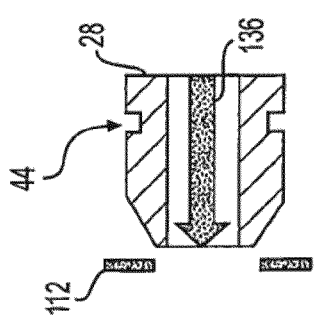 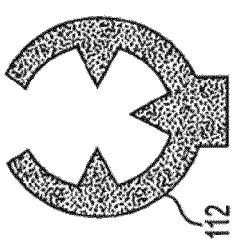 *FIG. 6A*
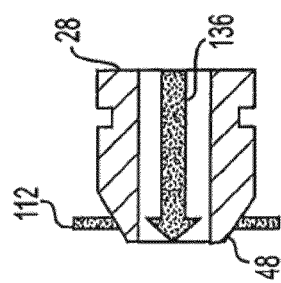 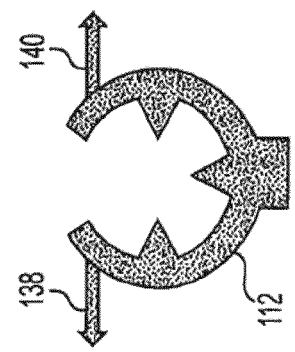 *FIG. 6B*
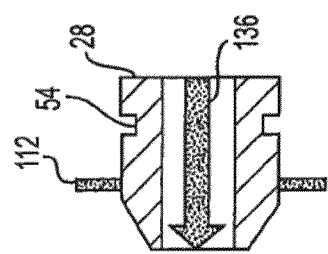 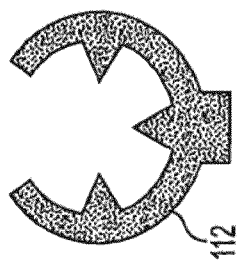 *FIG. 6C*
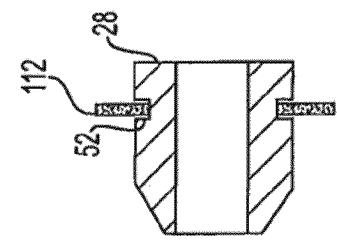 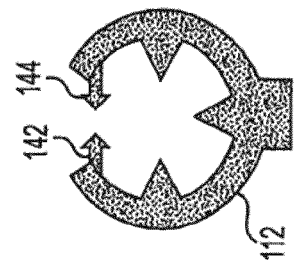 *FIG. 6D*

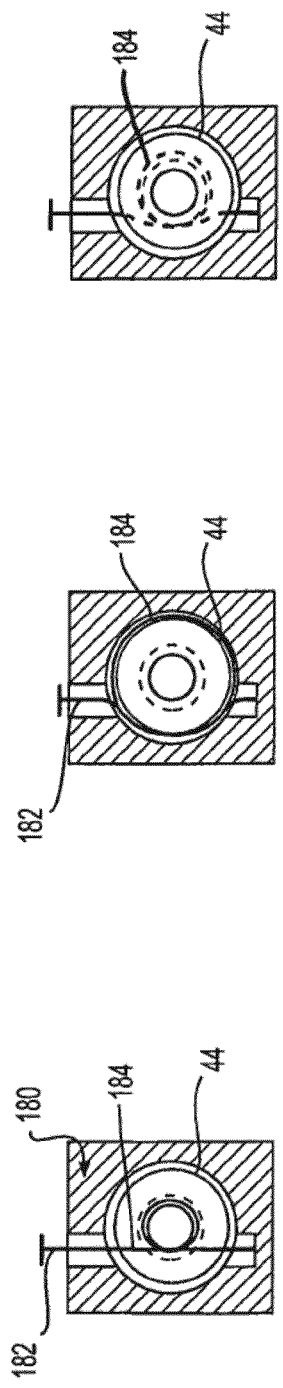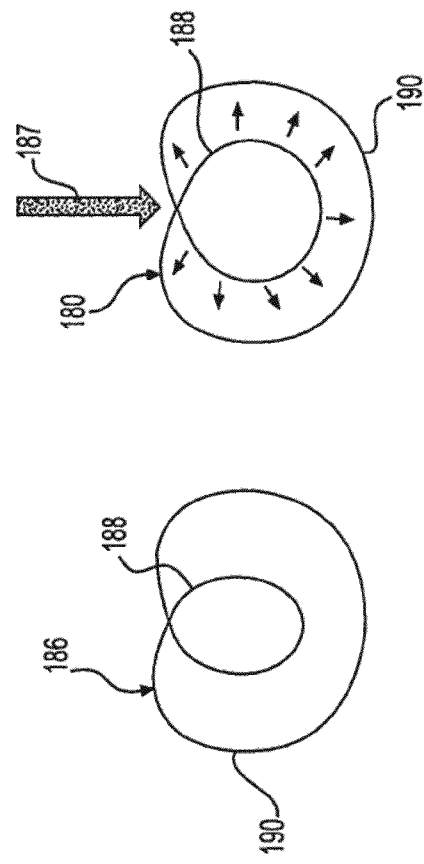

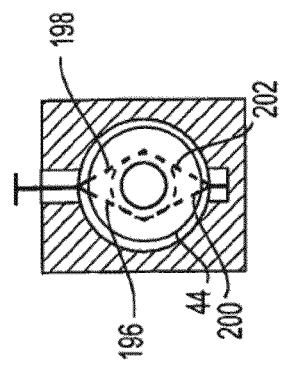
FIG. 12A
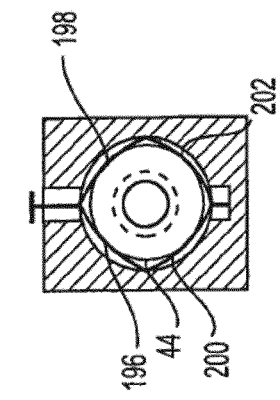
FIG. 12B
FIG. 12C
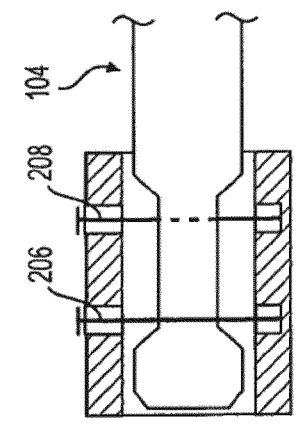
FIG. 13A
FIG. 13B
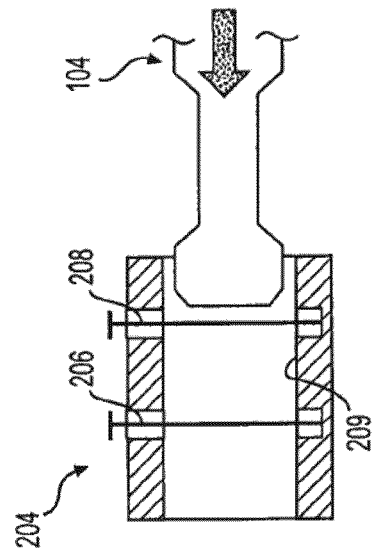
FIG. 13C

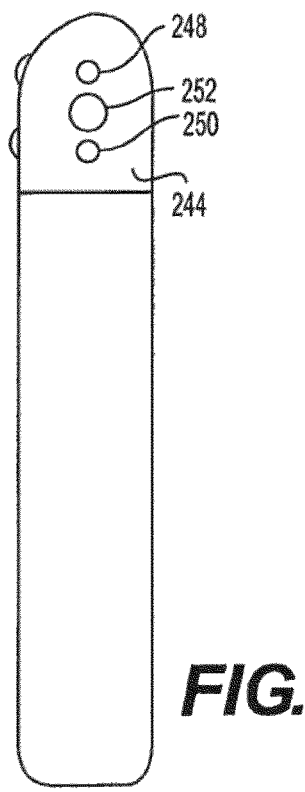
FIG. 16A
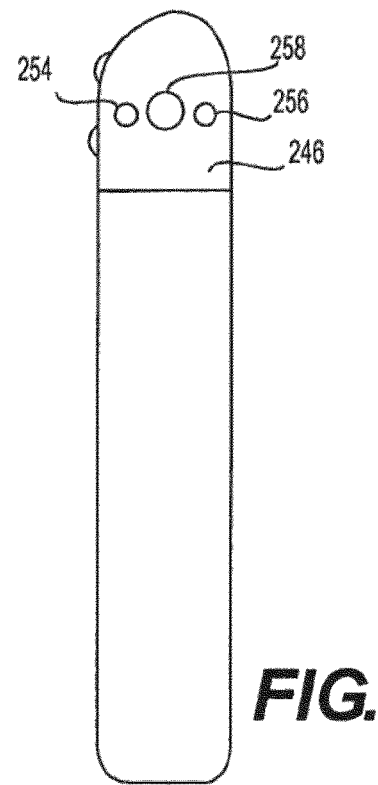
FIG. 16B
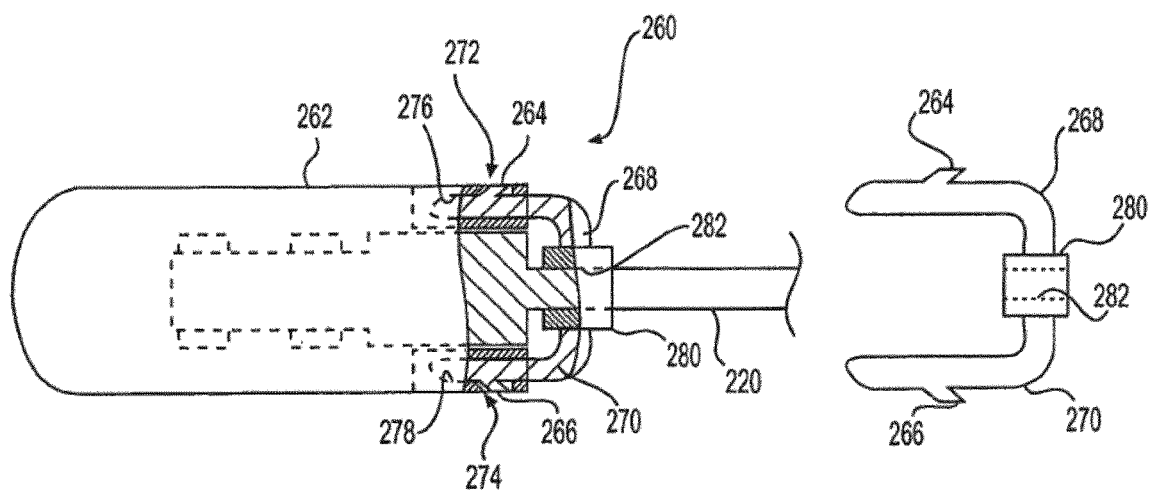
FIG. 17A   FIG. 17B

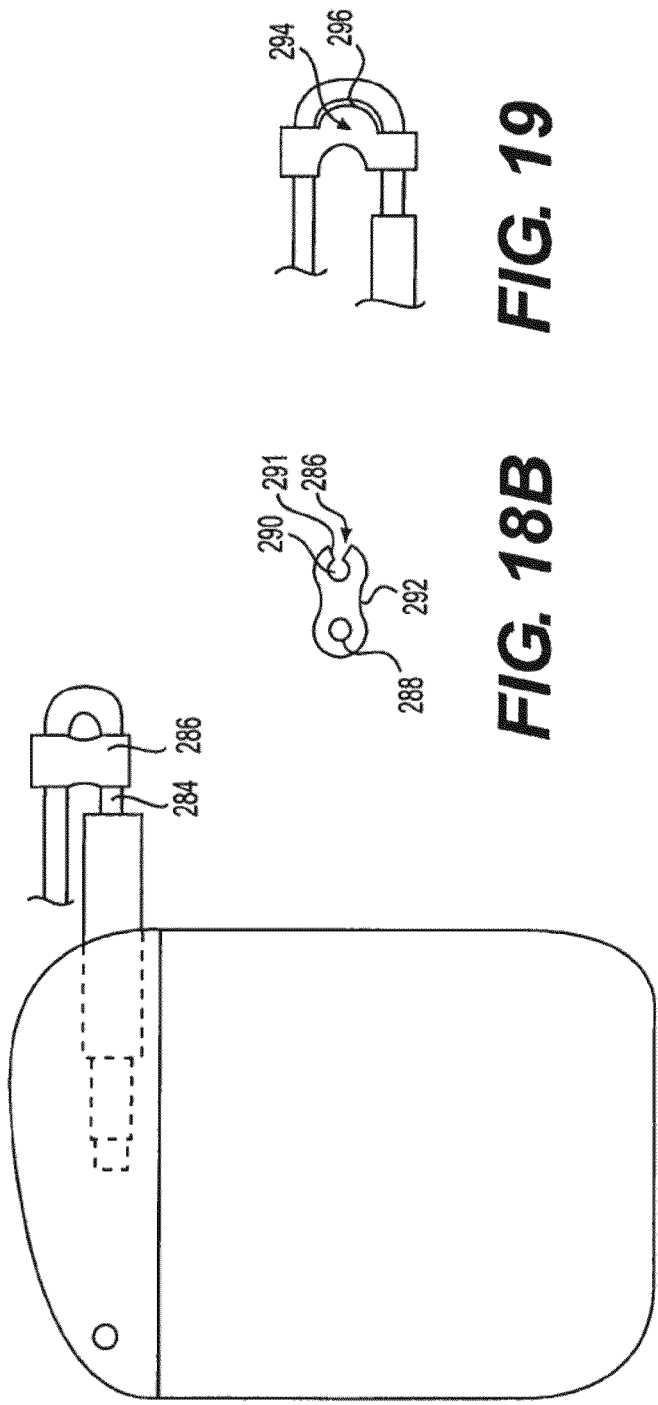

LEAD ENGAGEMENT DEVICES AND METHODS FOR ELECTRICAL STIMULATION AND/OR MONITORING SYSTEMS

CROSS-REFERENCE TO RELATED PATENT APPLICATION

This application is a continuation of U.S. patent application Ser. No. 14/694,848 filed on Apr. 23, 2015, the entire contents of which are incorporated herein by reference.

FIELD

Aspects of the present disclosure generally relate to implantable electrical stimulation and/or monitoring systems, such as, for example, implantable pulse generators (IPGs). More particularly, the present disclosure relates to mechanisms and methods for securing a lead (e.g., a stimulation or sensing lead) to an implantable electrical stimulation and/or monitoring system, such as an IPG.

BACKGROUND

IPGs typically may be used for stimulating and/or monitoring patient anatomy and/or physiology. To deliver a therapy or sense a biological parameter, for example, the IPG may be connected to one or more leads. Such a lead may be operably coupled to the IPG in any of number of ways. For example, a proximal end of a suitable lead may be configured for insertion into a header of the IPG. To secure the lead within the header, a user, for example, a surgeon, may tighten a plurality of set screws. In some embodiments, one or more of the set screws may mechanically secure the lead within the header, and one or more of the set screws may provide an electrical connection between the lead and electronics within the IPG.

Problems exist, however, with the use of set screws to secure the lead to the IPG. Over time, the set screws may rotate, loosen, or otherwise back off from the lead, which may result in insufficient contact between the lead and the electronics within the IPG. This may result in the patient failing to receive a desired electrical stimulation, or in difficulty monitoring patient physiology. While adding additional set screws may improve performance, as the number of set screws increases, tightening the set screws may become tedious. In addition, it may be difficult to keep track of which set screws have been tightened and which ones remain loose. Further, while tightening the set screws, one or more of the set screws may become damaged. For example, a surgeon may apply excessive forces which may strip a screw's threads and/or damage the screw's head. Though the use of set screws allows for providing tactile feedback to a user securing a lead, such feedback may not be provided if, for example, the lead is not inserted properly or the length of the screw is insufficient to contact the lead. Moreover, even when the lead is properly secured within the header, securing a lead to an IPG with set screws may prevent rotation of the lead, which may result in lead damage if the device and/or lead are rotated during normal patient activity.

To address these and other unmet needs, the present disclosure provides, by way of example and not necessarily limitation, systems, devices and methods for securing a lead to an IPG.

SUMMARY

According to an aspect of the present disclosure, an implantable pulse generator includes a housing, a header, and a retainer device. The housing includes circuitry and a battery. The header is coupled to the housing and includes a bore configured to receive an end of a lead, and a passage disposed transverse to the bore and extending between an exterior surface of the header and an anchor cavity that extends into the header from the bore. The header supports at least one electrical contact within the bore coupled to the circuitry. The retainer device includes a looped member arranged within the bore, a proximal end extending at least partially into the passage, and anchored at a distal end by the anchor cavity. The looped member has a first position defining a first loop diameter that permits egress of the lead into the bore and a second position defining a second loop diameter that occludes at least a portion of the bore and is configured to engage at least two opposing sides of the lead sufficiently to prevent egress of the lead from the bore. The first loop diameter is greater than the second loop diameter.

According to another aspect of this disclosure, an implantable pulse generator includes a housing having circuitry and a battery, a header coupled to the housing and including a bore configured to receive an end of a lead. The header supports at least one electrical contact within the bore coupled to the circuitry. A retainer device includes an annular member positioned within the bore, the annular member having a first position defining a first diameter concentric with the bore and permitting egress of the lead into the bore, and a second position defining a second diameter concentric with the bore and occluding at least a portion of the bore. The annular member is configured to engage the lead in the second position sufficiently to prevent egress of the lead from the bore, and the first diameter is greater than the second diameter.

According to another aspect of this disclosure, an implantable medical device includes a lead and an implantable pulse generator. The lead includes an engagement portion defining an exterior surface and an annular channel recessed into the lead from the exterior surface. The implantable pulse generator is coupled to the lead and includes a housing having circuitry and a battery, a header coupled to the housing and including a bore defining a bore axis and sized to receive the engagement portion of the lead and a passage disposed transverse to the bore axis, the header supporting at least one electrical contact within the bore coupled to the circuitry, and a retainer device positioned within passage and not fixed to the bore. The retainer device is retained within the passage to inhibited movement along the bore axis, and the retainer device is moveable between a first position permitting egress of the lead into the bore, and a second position engaging the channel of the lead to inhibit egress of the lead from the bore.

BRIEF DESCRIPTION OF THE DRAWINGS

The accompanying drawings, which are incorporated in and constitute a part of this specification, illustrate exemplary aspects of the present disclosure and together with the description, serve to explain the principles of the disclosure.

FIGS. 4A-4H are cross-sectional views of exemplary engagement devices, according to aspects of the present disclosure.

FIGS. 6A-6D illustrate the retainer device of FIG. 5A and an exemplary engagement device at progressive stages of engagement.

FIGS. 10A-10C illustrate axial views of an exemplary engagement device being inserted into another exemplary retainer device, according to another aspect of the present disclosure.

FIGS. 11A-11B illustrate front views showing another exemplary retainer device in expanded and contracted states, according to an aspect of the present disclosure.

FIGS. 12A-12C illustrate axial views of an exemplary engagement device being inserted into another exemplary retainer device, according to further aspect of the present disclosure.

FIGS. 13A-13C illustrate side views of another exemplary engagement device being inserted into another exemplary retainer device, according to an aspect of the present disclosure.

FIGS. 16A-16B are rear views of portions of exemplary IPG headers, according to aspects of the present disclosure.

FIG. 17A depicts a partial section view of portions of an exemplary IPG, lead, and an exemplary engagement device, according to an aspect of the present disclosure.

FIG. 17B illustrates the engagement device of FIG. 17A.

FIGS. 18A-18B illustrate a front view of an exemplary IPG, lead, and retainer clip, and an axial view of the retainer clip, according to another aspect of the present disclosure.

FIG. 19 depicts another exemplary retainer clip.

DETAILED DESCRIPTION

Reference now will be made in detail to the exemplary aspects of the disclosure, examples of which are illustrated in the accompanying drawings. Wherever possible, the same or similar reference numbering and lettering will be used throughout the drawings to refer to the same or like parts.

Figure 1:
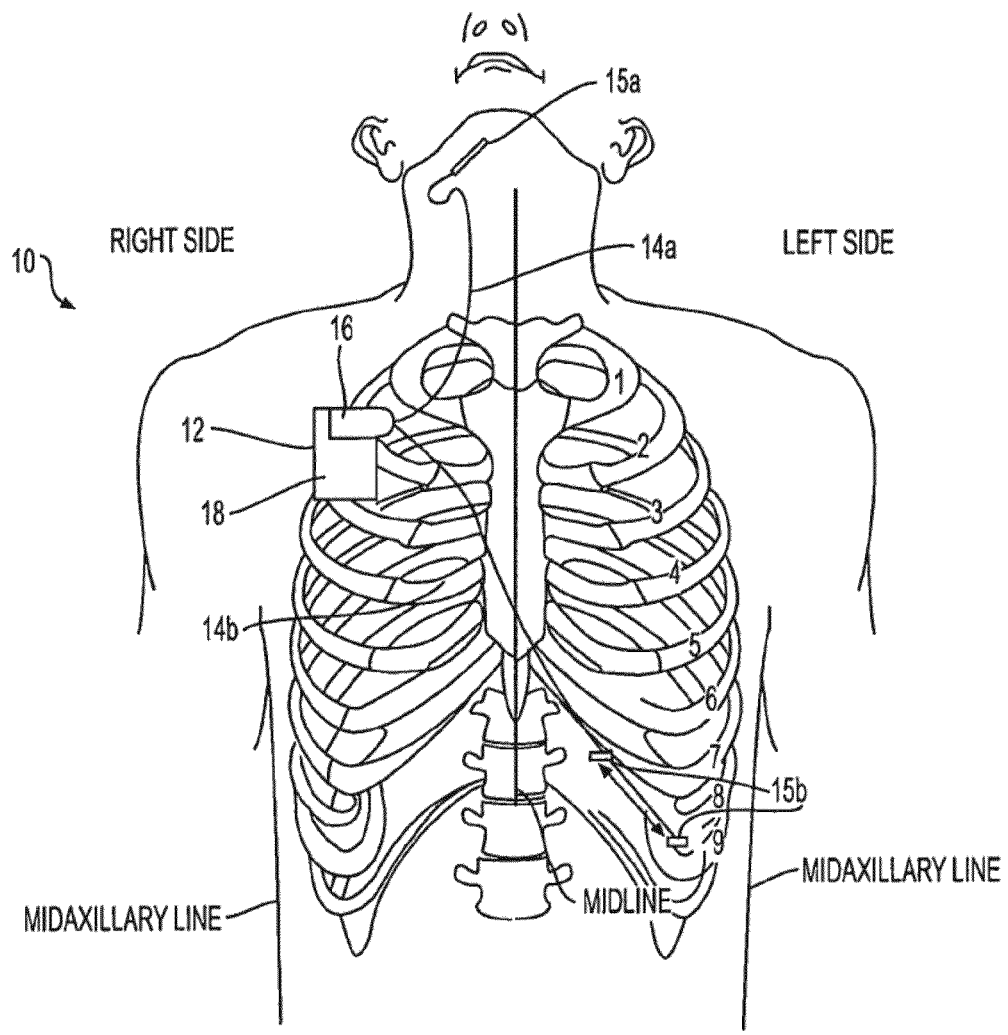
FIG. 1 illustrates portions of an exemplary IPG and lead implanted in a patient, according to an aspect of the present disclosure.

FIG. 1 shows an exemplary medical system 10 implanted in a patient and configured to provide electrical stimulation to and/or monitoring of the patient's body. Implantable components of the medical system 10 may include an IPG 12 and leads 14a, 14b operably coupled to IPG 12 to deliver a stimulation signal (via stimulation lead 14a) and/or to receive a sensor input (via sensing lead 14b). External components of the medical system 10 (not shown in FIG. 1) may include a patient/physician communications assembly configured to transmit signals to and receive signals from the implantable components of the medical system 10 when programming the implantable components, evaluating the performance of the implantable components, and/or conveying alerts or patient status updates. The IPG 12 may include a housing 18 that contains a battery and electrical components controlling the operation of the IPG 12, and the housing 18 may be configured to electrically interact with a stimulation delivered by the stimulation lead 14a and/or may be configured to facilitate the sensing of body signals or movements such as with the sensing of movement of the IPG 12 via an accelerometer disposed within the housing 18, or with the sensing of tissue pressure or temperature changes sensed via the surface of the housing 18. The IPG 12 also may include a header 16 that provides an interface between the internal components of the housing 18 and the leads 14a, 14b via one or more ports of the header that are configured to receive the proximal ends of the leads 14a, 14b when the system is assembled and implanted. The leads 14a, 14b may include proximal ends that couple to the header 16 of the IPG 12 and distal ends that each support a patient-interface component that may be a nerve cuff 15a at the distal end of the stimulation lead 14a and/or a sensor 15b at the distal end of the sensing lead 14b. The patient-interface component may be a nerve cuff 15a that may be disposed to delivery energy to a nerve or muscle tissue of the patient, such as to the hypoglossal nerve in the treatment of sleep apnea (as illustrated in FIG. 1) or to the vagus nerve in the treatment of epilepsy (not shown). The patient-interface component also may be a sensor 15b that may be disposed to receive biological signals from the patient's body relating to nerve activity, inter-tissue pressure changes, movement of tissue, changes in impedance of tissue, and temperature changes. Although the embodiment illustrated in FIG. 1 shows an IPG configured to treat sleep apnea via stimulation provided to the hypoglossal nerve and via a sensing of respiration provide from a sensor, it can be appreciated that the IPG 12 may be configured to deliver different therapies to the patient and/or to sense or monitor a variety of patient signals. For example, IPG 12 may be configured as any of a spinal cord stimulator, brain stimulator, peripheral nerve stimulator, vagal nerve stimulator, occipital nerve stimulator, hypoglossal nerve stimulator, gastric stimulator, pacemaker, defibrillator, or the like. Leads 14a, 14b may be any suitable lead configured to, for example, deliver an electrical stimulation therapy and/or sense one or more biological parameters, including, for example, impedance, pressure, etc.

As illustrated in FIG. 1, IPG 12 and leads 14a, 14b may be implanted in a patient with the IPG 12 disposed in a subcutaneous pocket and with leads 14a, 14b disposed in subcutaneous tunnels that position the distal ends of the leads 14a, 14b at the desired sites for delivering therapy or acquiring a sensed signal. For example, the proximal ends of leads 14a, 14b may be mechanically and/or electrically connected to IPG 12 and the distal end of the stimulation lead 14a may be placed on or near the hypoglossal nerve and the sensing lead 14b may be placed between ribs of the rib cage as illustrated in FIG. 1. In another example, the system 10 may have only a single stimulation lead 14 or the system 10 may have a single lead 14 provide the functions of the stimulation lead 14a and sensing lead 14b that is placed, for example, on or near the vagus nerve. Those of ordinary skill in the art will recognize that the distal ends of leads 14a, 14b may be positioned at any suitable location within a patient.

Figure 2:
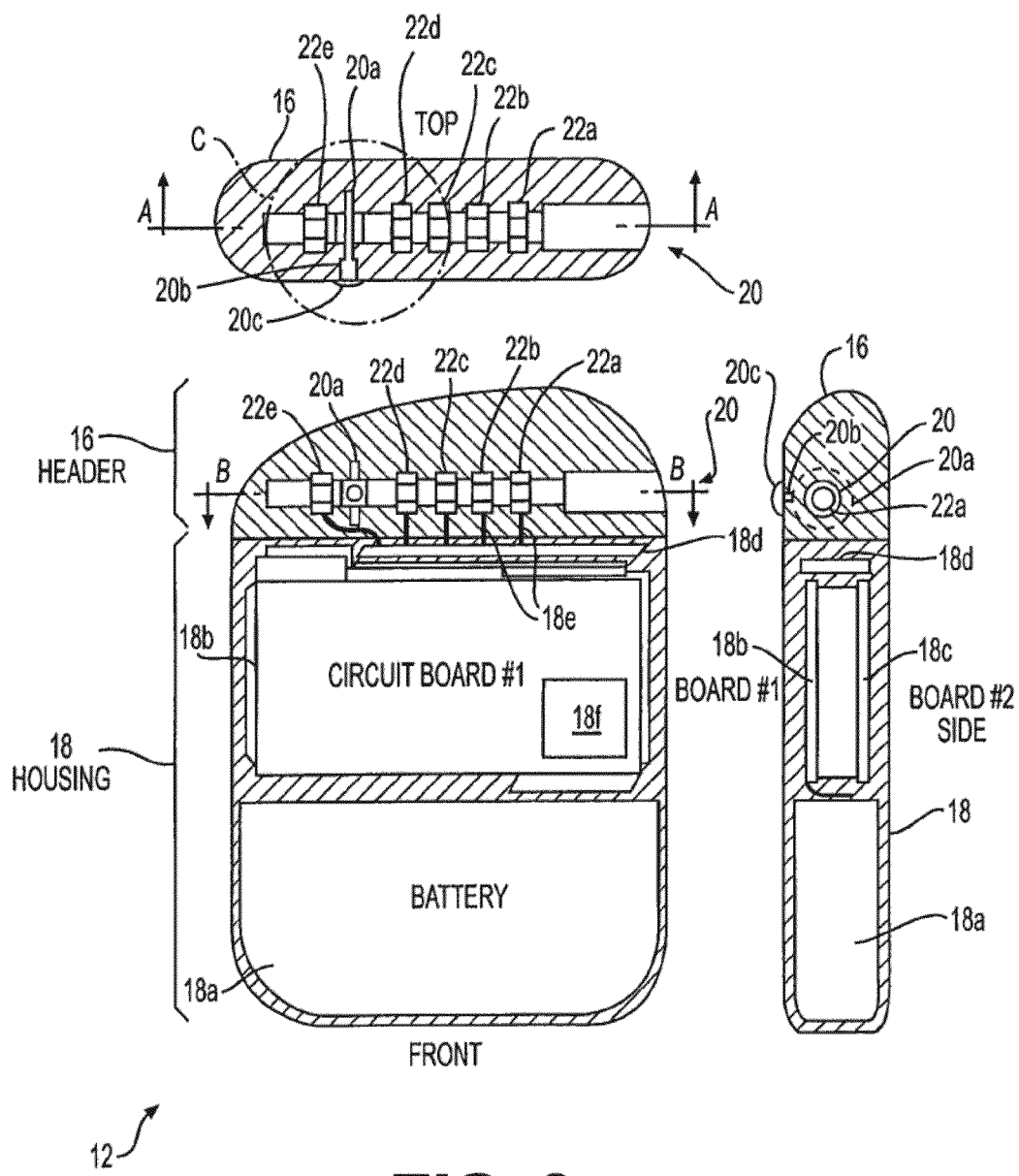
FIG. 2 illustrates three views of the IPG of FIG. 1, showing an interior region of a header of the IPG.

FIG. 2 illustrates three views of an another embodiment of the IPG 12 configured for use with a single lead 14 instead of the two leads 14a, 14b illustrated in FIG. 1. The three views illustrated in FIG. 2 include a cross-sectional top view of a single-lead IPG 12 showing internal features of the header 16, a cross-sectional front view of the IPG 12 with the cross-section taken along a partition line A shown in the top view, and a partial cross-sectional side view of the IPG 12 having only the housing 18 shown in the cross-section. The cross-sectional top view of FIG. 2 is taken along a partition line B shown in the front view. As illustrated in FIG. 2, housing 18 may include a battery 18a and one or more circuit boards 18b, 18c, and 18d that are coupled to each other and/or the battery 18a and that have wiring 18e leading from the boards 18b-18d into the header 16. The circuit board 18b may support an accelerometer 18f.

Figure 3:
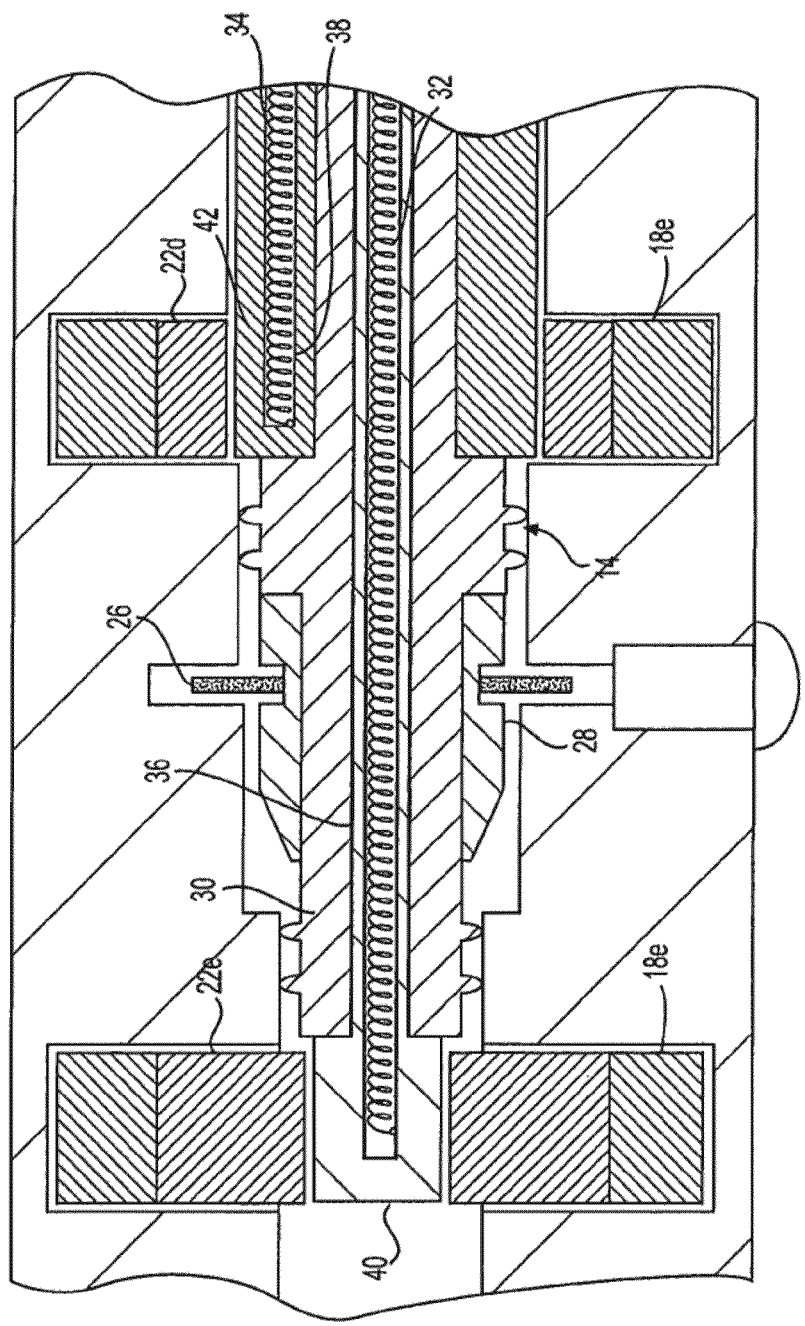
FIG. 3 is a cross-sectional view of another embodiment of a header and lead, showing an enlarged view of the interior region of the header of the IPG, including an exemplary engagement device and an exemplary retainer device.

As further illustrated in FIG. 2, header 16 may include a bore 20 for receiving the proximal end portion of a lead 14 therein. One or more electrical contacts 22a-22e may be positioned in and/or around an internal surface of bore 20. The electrical contacts 22a-22e may be electrically connected to the circuitry within IPG 12 via the wiring 18e. An exemplary electrical contact may include, for example, a BAL CONN™ electrical contact or SYGNUS™ seal and electrical contact system available from Bal Seal Engineering, Inc. As those of ordinary skill in the art will appreciate, however, any other suitable electrical contact that may provide at least one of an electrical and/or mechanical connection may be used with the principles of the present disclosure. In the embodiment illustrated in FIG. 2, the contacts 22a-22e each have an interior surface that is biased inwardly to compress against a lead once inserted within the contact. As illustrated, each contact 22a-22e is in a relaxed state that advances the interior surface to an inward-most position. As can be appreciated, each of the interior surfaces of the contacts 22a-22e will move outwardly away from a center line of the bore 20 when pushed outward by the introduction of an appropriately-sized lead, as illustrated in FIG. 3.

The bore 20 may include a cavity 20a disposed along a length of the bore 20 either between the contacts 22a-22e (as shown in FIG. 2) or disposed at an end of the bore (not shown). The cavity 20a may be circular as shown in the side view of FIG. 2 and have a diameter that is greater than an internal diameter of the bore 20, as shown in the top and side views of FIG. 2. The cavity 20a may also be a portion of the bore that has an increased diameter as compared to an initial diameter of the bore 20 located where the bore 20 terminates at the external surface of the header 16. The cavity 20a may couple to a passage 20b disposed transverse to the bore 20 that provides access to the outer peripheral surface of the cavity from a side of the header 16. As can be appreciated, in the illustrated configuration the cavity 20a has two pathways to the exterior of the header 16; a first pathway through the bore 20 and a second pathway through the passage 20b. The passage 20b may be occluded with a plug 20c or another obstructing material.

Figure 2A:
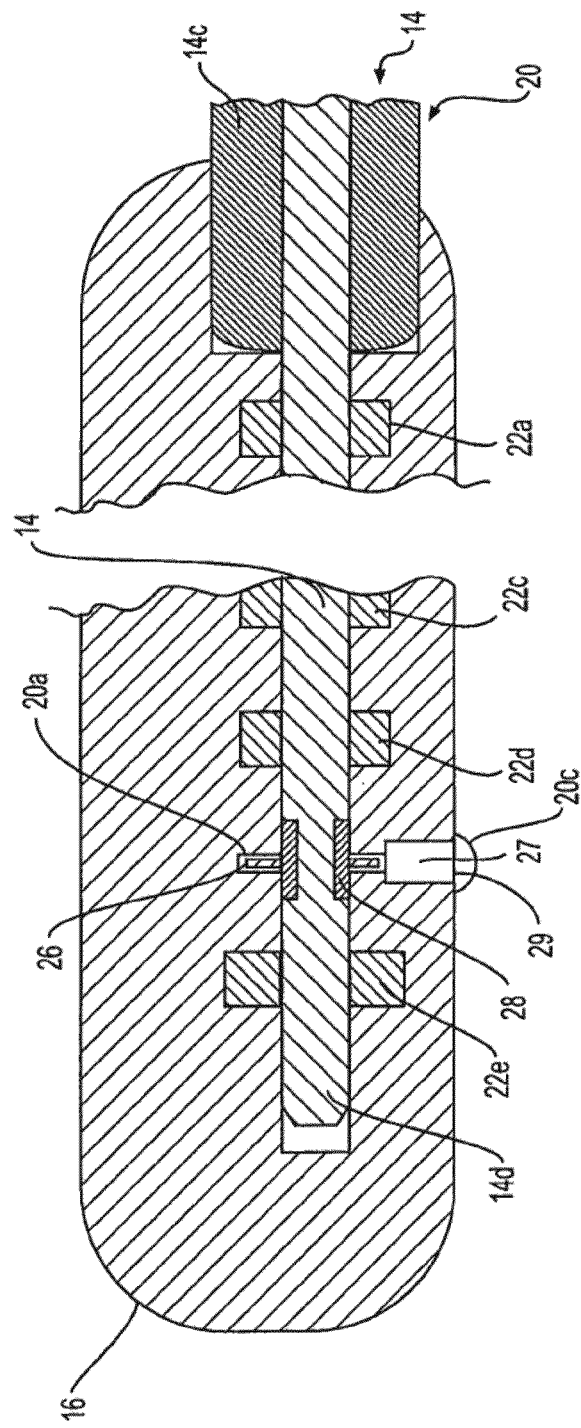
FIG. 2A illustrates portions of the IPG of FIG. 1 and an exemplary lead inserted in a header of the IPG.

FIG. 2A illustrates a close-up cross-sectional view of a portion C of the header 16 shown in the top view of FIG. 2, with the header 16 again shown in the cross-section and with a lead 14 and a retainer device 26 shown in the cross-section in an inserted position within the header 16. FIG. 2A further illustrates a placement of a proximal end of the lead 14 within the bore 20 of the header 16 and illustrates a placement of a retainer device 26 within the cavity 20a. The proximal end of the lead 14 includes a compressible insulated portion 14c configured to provide a grip by which to hold the lead 14 when inserting the proximal end of the lead 14 into the bore 20, and configured for insertion into the initial portion of the bore 20 so as occlude the bore 20 to prevent the ingress of fluid into the bore 20 and to provide a friction fit that helps to secure the lead 14 within the bore 20. The retainer device 26 is configured to receive and/or secure an engagement portion 28 of the lead 14 and may be positioned partially in and/or around the internal surface of bore 20 within the cavity 20a. According to one aspect, retainer device 26 may be positioned between first and second electrical contacts 22d and 22e. The retainer device 26 may be electrically isolated from one or more portions of header 16, and/or from one or more portions of lead 14. The engagement portion 28 of lead 14 may be electrically isolated from the remainder of the lead 14. The engagement portion 28 of the lead 14 may be a metal cladding disposed over a lead body 14d, and the lead body 14d may be an elastomer or an elastomer supporting a series of electrical pathways extending between the proximal and distal ends of the lead 14. The metal cladding of the engagement portion 28 may be configured to oppose an inward pressure exerted on the lead 14 by the inward compression of the retainer device 26. Retainer device 26 also may be electrically isolated from electrical contacts 22a-22e of header 16, and/or from electrical contacts or electrodes 40 and 42 (FIG. 3) integrally formed on lead 14. Further, retainer device 26 may include any feature or combination of the features described in connection with the exemplary embodiments discussed below in more detail.

Though only one retainer device 26 is depicted in FIG. 2A, multiple retainer devices 26 may be provided with corresponding cavities 20a disposed to hold the retainer devices 26 in place along the length of the bore 20. Additionally, header 16 may include a recess 27 extending between the cavity 20a and the exterior surface of the header 16 through which the user may access retainer device 26 within the cavity 20a. In order to prevent biological material from entering into header 16 through the passage provided by recess 27 between the bore 20 and the external environment of the header, recess 27 may be covered with material forming a plug or septum 20c configured to occlude and/or seal recess 27, or covered with a material that is continuous with the exterior of the header 16. Septum 20c may be punctured or removed to open the passage leading to recess 27 and to cavity 20a, and the plug or septum 20c may be configured to be resealable or repairable so as to close any puncture or breach of the seal. For example, septum 20c may include a silicone seal covering recess 27. In other embodiments, septum 20c may be a cap or plug and configured to allow full or partial removal of the cap or plug 20c so as to allow reuse and reinsertion of the same cap or plug 20c into a position that occludes the pathway to the bore 20. In yet another embodiment, the cap 20c may have threads or a high-friction surface that provides a sealing engagement between the cap 20c and the walls of the recess 27.

The engagement portion 28 may be formed as a component of the lead 14 or provided as an engagement device 28 disposed over the exterior of the lead 14. In some embodiments, engagement device 28 may be configured to frictionally engage retainer device 26 with the friction maintained by an inwardly-pressing force provided by the retainer device 26 that is generated when the retainer device 26 is deflected or expanded to accommodate the insertion of the engagement device 28 within the retainer device 26. Though FIG. 2A depicts that the engagement device 28 may be positioned distally of the proximalmost end of lead 14, those of ordinary skill will understand that the engagement device 28 may be positioned at any suitable position along the proximal end of lead 14 including the proximalmost end of the lead 14. Engagement device 28 may be electrically isolated from one or more portions of lead 14, and/or from one or more portions of header 16. For example, engagement device 28 may be electrically isolated from electrical contacts or electrodes 40 and 42 (FIG. 3) on lead 14, and/or from electrical contacts 22a-22e of header 16. Further, engagement device 28 may include any feature or combination of the features described in connection with the exemplary embodiments discussed below in more detail.

Figure 2B:
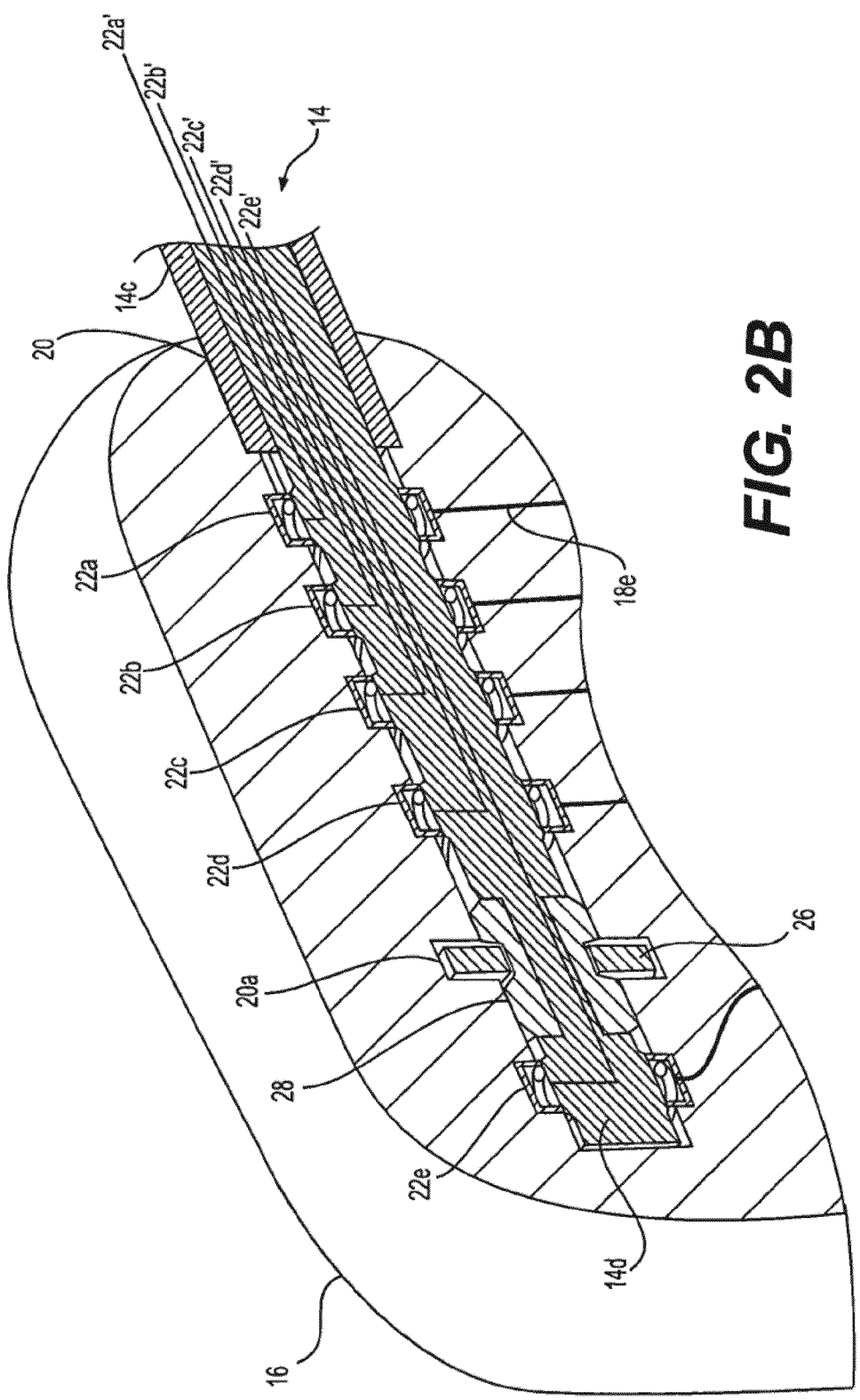
FIG. 2B illustrates portions of an alternative header and lead configuration similar to the embodiment of FIG. 2A.

FIG. 2B is an illustration of another embodiment of the proximal end of a lead 14 disposed within a bore 20 of a header 16, shown in an isometric cross-section view that provides additional details regarding the interaction between the lead 14 and the interior of the bore 20. As illustrated, the header 16 supports the contacts 22a-22e that are dispose to provides an electrical connection between the wiring 18e and the exterior surfaces of the proximal end of lead 14. As can be appreciated, the proximal end of the lead 14 may include multiple surfaces configured to align with each the contacts 22a-22e so as to provide a collective or separate electrical connection between the contacts 22a-22e and one or more interface components (not shown) disposed at the distal end of the lead 14 (not shown). The electrical connection between the contacts 22a-22e and the proximal end of the lead 14 is shown schematically by electrical pathways 22a'-22e', each of which corresponds to an electrical connection made with the contacts 22a-22e.

FIG. 3 illustrates a closer cross-sectional view of an exemplary engagement between another embodiment of the header 16 and a proximal end of the lead 14 when the lead 14 is disposed within the bore 20. As illustrated, lead 14 may include a tubular jacket 30 with one or more electrical conductors 32 and 34 extending co-axially within the lead 14. One electrical conductor 32 may extend within a central passage 36 through jacket 30 from a proximal end to a distal end (not shown) that may engage an interface device (not shown) so as to provide a first electrical connection between the proximal and distal ends of the lead 14. Another electrical conductor 34 may extend within a peripheral passage 38 in jacket 30 from a proximal end to a distal end (not shown) that may engage the same interface device coupled to conductor 32 (not shown) or to another interface device (not shown) so as to provide a second electrical connection between the proximal and distal ends of the lead 14. Jacket 30 may include any suitable non-conductive material, including, but not limited to, extruded silicone. Jacket 30 optionally may have a covering of co-extruded polyurethane to, for example, improve durability or provide non-conductivity. It is contemplated that jacket 30 may be non-conductive, and may electrically isolate engagement and retainer devices 26 and 28 from electrical contacts (such as contacts 22d and 22e) and/or from electrical contacts 40 and 42.

Conductors 32 and 34 may include braided and/or coiled wires and may include an exterior tubing surrounding the coiled wires as illustrated in FIG. 3. The number of conductors may be adjusted depending on the intended application of lead 14 and the desired connectivity between the proximal and distal ends of the lead 14. For example, each of conductors 32 and 34 may be individually connected to an electrical contact 40 or 42 disposed on a proximal end portion of lead 14. In another embodiment, a single conductor may be connected to two or more electrical contacts 40 and 42 disposed on a proximal end of lead 14. Portions of jacket 30 may be removed at distal and/or proximal portions of the lead 14 to expose electrodes (not shown) and/or electrical contacts 40 and 42, respectively.

With further reference to the embodiments illustrated in FIGS. 2A, 2B and 3, the header 16 is provided with the cavity 20a having a shape that contains the axial movement of a retainer device 26 within the bore 20 while allowing rotational movement about an axis defined by the bore 20. The retainer device 26 engages the exterior of the lead 14 so as to likewise prevent undesirable axial movement of the lead 14 through the bore 20 once the engagement between the retainer device 26 and the lead 14 is achieved. The retainer device 26 engages the exterior of the lead 14 by deflecting or expanding an inner diameter or dimension of the retainer device 26 to receive the lead 14 when inserted into the bore 20 until reaching an engagement portion 28 of the lead 14 which is configured to provide an engagement with the retainer device 26. In the embodiment illustrated in FIG. 3, the exterior surface of the engagement portion 28 may include a groove or channel configured to receive the inner surface of the retainer device, and the channel or groove may have edges that further inhibit the axial movement of the lead 14 or engagement portion 28 relative to the retainer device 26. The channel or groove may also have a bottom that may firmly engage the inner surface of the retainer device 26 when the expanded or deflected retainer device 26 returns to its original configuration or, alternatively, the depth of channel or groove may be deep enough so that there is little or no engagement between the inner surface of the retainer device 26 and the bottom of the channel or groove which would provide a floating engagement between the retainer device 26 and the engagement portion 28. As can also be seen in the embodiment of FIG. 3, the exterior surface of the engagement portion 28 may include a chamfered or angled edges that facilitates the insertion of the lead 14 through the interior of the retainer device 26 when the lead 14 is inserted into the bore 20. As can be further appreciated, the chamfered or angled edges of the engagement portion 28 (such as those shown in FIGS. 4A-4H) may be configured to have a diameter or dimension that is smaller than the inner opening of the retainer device 26 and the chamfered or angled surface may be configured to deflect or expand the inner opening of the retainer device 26 as the lead 14 is introduced into the bore 20.

With reference to FIGS. 4A-4H, engagement device 28 may include one or more of the features described in connection with the exemplary embodiments depicted in the figures. For example, in one exemplary embodiment of an engagement device 44 depicted in FIG. 4A, a proximal end face 46 may define a proximal end of engagement device 44. A chamfered or tapered portion 48 may extend distally from proximal end face 46, with a diameter of tapered portion 48 increasing in a direction moving away from proximal end face 46. The surface of tapered portion 48 may have a positive or rising slope relative to a central longitudinal axis of engagement device 44. Tapered portion 48 may be configured to deflect and/or expand retainer device 26 when inserted into retainer device 26 (e.g., to facilitate further insertion by moving retainer device 26 out of the way), and to allow retainer device 26 to move back toward an undeflected and/or contracted state when extracted from retainer device 26 (e.g., to facilitate extraction by the force exerted on tapered portion 48 by retainer device 26), as described in greater detail below.

From a distal end of tapered portion 48, a cylindrical portion 50 may extend distally. Unlike tapered portion 48, cylindrical portion 50 may have a constant diameter. The outer surface of cylindrical portion 50 may extend parallel to the central longitudinal axis (not shown) of engagement device 44. Cylindrical portion 50 may maintain retainer device 26 in a deflected state when engaging retainer device 26.

Engagement device 44 also may include a shoulder 52 where cylindrical portion 50 transitions to another cylindrical portion 54, cylindrical portion 54 extending distally from cylindrical portion 50 and having a smaller diameter than cylindrical portion 50. Shoulder 52 may include a distally-facing surface that extends radially in, for example, a direction perpendicular to the central longitudinal axis of engagement device 44. During insertion of engagement device 44 into retainer device 26, shoulder 52 may allow retainer device to move rapidly from the deflected and/or expanded state to the undeflected and/or contracted state. Retainer device 26, upon coming into contact with cylindrical portion 54, may produce audible and/or tactile feedback experienced by the user as the inner surface of the retainer device 26 resumes a less expanded or deflected configuration as it falls into the channel or groove defined by cylindrical portion 54 and shoulders abutting the cylindrical portion 54. Once retainer device 26 is in contact with cylindrical portion 54, shoulder 52 may inhibit extraction of engagement device 44 from retainer device 26 by abutting a proximally-facing surface of retainer device 26.

Engagement device 44 also may include another shoulder 56 where cylindrical portion 54 transitions to another cylindrical portion 58 having a larger diameter. Shoulder 56 may be similar to shoulder 54, except shoulder 56 may define a proximally-facing surface. Shoulder 52, cylindrical portion 54, and shoulder 56 may form a recessed portion or groove for receiving a portion of retainer device 26. As such, shoulder 52 may inhibit engagement device 44 from being extracted from retainer device 26, and shoulder 56 may inhibit engagement device 44 from being inserted further into retainer device 26 by abutting a distally-facing surface of retainer device 26. Together, shoulders 52 and 56 may ensure proper positioning and securement of engagement device 44 in retainer device 26 by providing surfaces that facilitates proper positioning and by providing feedback to a user when proper positioning is achieved.

Engagement device 44 also may include a bore 60 configured to receive the lead body 14d and/or an electrical conductor extending through lead 14. Bore 60 may extend longitudinally through a central portion of engagement device 44. As shown in FIG. 3, lead 14 may be fixedly attached to the surface of engagement device 44 defining bore 60 by friction-fit, use of adhesive(s), and/or application of any other suitable form of attachment. Alternatively, engagement device 44 may be integrally formed with lead 14. In another embodiment, engagement device 44 may be composed of two halves that come together to form an entire engagement device 44 about an exterior of the lead body 14d.

In another exemplary embodiment depicted in FIG. 4B, an engagement device 62 may include a chamfered or tapered portion 64 configured to receive the retainer device 26. A diameter of tapered portion 64 may decrease in the distal direction. The surface of tapered portion 64 may have a negative or falling slope relative to a central longitudinal axis of engagement device 62. Tapered portion 64 may be configured to allow retainer device 26 to gradually move back toward an undeflected and/or contracted state when inserted into retainer device 26 (e.g., to facilitate insertion due to the force exerted on tapered portion 64 by retainer device 26), and to deflect and/or expand retainer device 26 when the lead 14 is extracted from retainer device 26 by the distal movement of the lead 14 (e.g., to facilitate further extraction by moving retainer device 26 out of the way). Engagement device 62 may include a shoulder 66 at a transition between tapered portion 64 and a cylindrical portion 68. Tapered portion 64 and shoulder 66 may form a recessed portion or groove for receiving retainer device 26.

In yet another exemplary embodiment of an engagement device 70 depicted in FIG. 4C, shoulder 66 and cylindrical portion 68 of engagement device 62 may be replaced with a cylindrical portion 72. It should be appreciated that a portion of lead 14 (FIG. 3), such as a proximally-facing surface of jacket 30, may be positioned at the distal end of engagement device 70. The proximally-facing surface of jacket 30, cylindrical portion 72, and a tapered portion 74 may form the recessed portion or groove for receiving retainer device 26.

With reference to the exemplary embodiment of an engagement device 76 depicted in FIG. 4D, shoulder 56 and cylindrical portion 58 of engagement device 44 may be replaced with a cylindrical portion 78. Cylindrical portion 78 may be similar to cylindrical portion 72, and together with a shoulder 80 and the proximally-facing surface of jacket 30 (FIG. 3), a recessed portion or groove may be formed for receiving retainer device 26.

With reference to another exemplary embodiment depicted in FIG. 4E, an engagement device 82 may be similar to engagement device 44, except shoulder 52 may be replaced with a tapered portion 84 having a negative or falling slope. While shoulder 52 may inhibit extraction of engagement device 44 from retainer device 26, tapered portion 84 may facilitate extraction by urging retainer device 26 into a deflected and/or expanded state when, for example, a distal pulling force is applied on lead 14.

In the exemplary embodiment of FIG. 4F, an engagement device 86 may be similar to engagement device 44, except tapered portion 48 may be omitted. In this embodiment, the diameter of a proximal end face 88 may correspond to the diameter of a cylindrical portion 90. Proximal end face 88 may inhibit insertion of engagement device 44 into retainer device 26. As will be described in more detail below, the user may apply a force to retainer device 26 to move it into a deflected and/or expanded state, thereby permitting insertion of engagement device 86 into retainer device 26.

In still another exemplary embodiment depicted in FIG. 4G, an engagement device 92 may include, going from a proximal end to a distal end, a positive-sloped tapered portion 94, a negative-sloped tapered portion 96, another positive-sloped tapered portion 98, a cylindrical portion 100, and a negative-sloped tapered portion 102. Tapered portions 96 and 98 may form a recessed portion or groove for receiving retainer device 26. Additionally or alternatively, tapered portion 102, together with the proximally-facing surface of jacket 30 (FIG. 3), may form the recessed portion or groove for receiving retainer device 26 or an additional retainer device.

With reference to the exemplary embodiment depicted in FIG. 4H, an engagement device 104 may be similar to engagement device 44, except engagement device 104 may include a negative-sloped tapered portion 106 in place of shoulder 52, a positive-sloped tapered portion 108 in place of shoulder 56, and an elongated cylindrical portion 110 in place of cylindrical portion 54. Tapered portion 106, cylindrical portion 110, and tapered portion 108 may form an elongated recessed portion or groove for receiving retainer device 26, or multiple retainer devices, as will be described in more detail below.

The dimensions and/or slopes of the above-described portions of the engagement devices depicted in FIGS. 4A-4H may differ from those that are depicted in the drawings. For example, the width of any of the recessed portions or grooves corresponding to the engagement devices depicted in FIGS. 4A-4H may be sized to receive portions of retainer device 26, with little or no gaps between surfaces of the recessed portions or grooves and the received portions of retainer device 26. This sizing may firmly secure the engagement devices depicted in FIGS. 4A-4H in retainer device 26 with little or no movement between the devices following securement. It should also be appreciated that the tapering, cylindrical, and/or shoulder portions of the engagement devices depicted in FIGS. 4A-4H may extend annularly about the engagement devices depicted in FIGS. 4A-4H, allowing the engagement devices depicted in FIGS. 4A-4H to rotate relative to retainer device 26 without losing or otherwise breaking electrical coupling between electrical contacts of lead 14 and header 16, even as relative longitudinal movement is inhibited or prevented. This rotational ability may help reduce or eliminate the build-up of torsional stress in lead 14. Alternatively, one or more of the tapering, cylindrical, and/or shoulder portions may extend only partially around the engagement devices depicted in FIGS. 4A-4H, allowing partial rotation of the engagement devices depicted in FIGS. 4A-4H relative to retainer device 26, in instances where full rotation is not desired by the user.

With regard to the construction of the engagement devices depicted in FIGS. 4A-4H, one of ordinary skill would appreciate that any of the depicted engagement devices may be made of metal, polymer, and/or any suitable material or combination of materials. It is contemplated that the material(s) for any of the disclosed engagement devices may be selected such that the engagement devices may possess a greater hardness or rigidity than retainer device 26. This may enhance the ability of the disclosed engagement devices to deflect retainer device 26 during insertion of the engagement devices into retainer device 26, and/or extraction of the engagement devices out of retainer device 26. It is further contemplated that the disclosed engagement devices may be made of or coated with an insulating or non-conductive material to ensure that electrical energy is not conducted through the engagement devices.

Figure 5B:
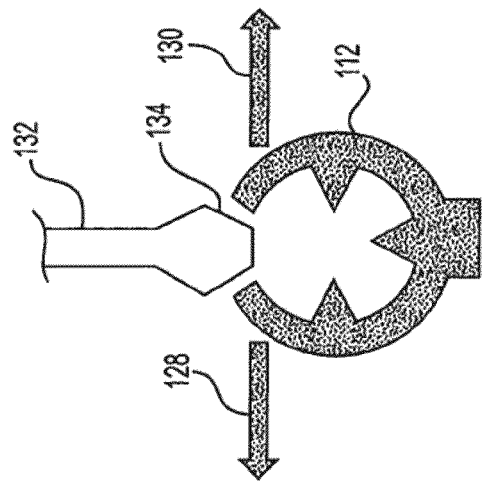
FIG. 5B is an axial view of the retainer device of FIG. 5A and an exemplary tool for manipulating the retainer device.
Figure 5A:
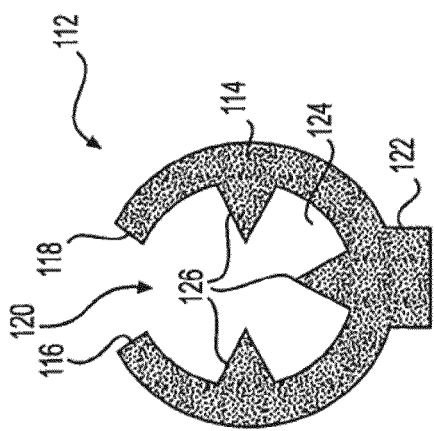
FIG. 5A is an axial view of an exemplary retainer device, according to an aspect of the present disclosure.

FIGS. 5A-5B provide a plan view of an exemplary retainer device 26 that may be used in any of the embodiments illustrated in FIGS. 2A-4H. The retainer device illustrated in FIGS. 5A and 5B may include one or more of the features described in connection with the exemplary embodiment illustrated in those figures. In the exemplary embodiment illustrated in FIGS. 5A-5B, a retainer device 112 may include a substantially ring-like configuration. For example, as shown in FIG. 5A, retainer device 112 may include a circular or annular cross-sectional configuration. Those of ordinary skill will recognize that retainer device 112 may include any suitable configuration, including, for example, elliptical, rectangular, triangular, and/or polygonal. Retainer device 112 may include a base 114 defining an incomplete circular cross-sectional configuration. Specifically, base 114 may include first and second ends 116 and 118 disposed on opposing sides of a gap 120 extending along one side of retainer device 112. The size of gap 120 may increase as retainer device 112 is moved toward a deflected and/or expanded state, and may decrease as retainer device 112 returns to an undeflected and/or contracted state, as will be described in further detail below.

Retainer device 112 also may include a hub 122. Hub 122 may extend radially away from base 114, on a side of retainer device 112 opposite to gap 120. Hub 122 may include any suitable configuration and/or shape. In some embodiments, hub 122 may be configured to hold retainer device 112 in position inside bore 20 of header 16. For example, hub 122 may engage an opening, slot, or groove (not shown, see FIGS. 2-3) on an interior surface of header 16 that forms bore 20 and or cavity 20a. One or more surfaces defining the opening, slot, groove, or cavity 20a may restrict rotational and/or longitudinal movement of hub 122 relative to bore 20, thereby restricting movement of retainer device 112.

Retainer device 112 may define a central longitudinal opening 124 extending through base 114. Opening 124 may include any suitable configuration and/or shape. In some embodiments, base 114 may include one or more engaging elements 126 extending away from base 114 into opening 124. Engaging elements 126 may be configured to engage an outer surface of engagement device 28 when engagement device 28 is positioned within opening 124. The engagement elements 126 may be configured to engage the channel or groove defined by the exterior surfaces of the engagement portion 28. Engaging elements 126 may include any suitable configuration, as explained in further detail below.

In one embodiment, engaging elements 126 may be configured as the teeth shown in FIG. 5A. The teeth of FIG. 5A may include a substantially triangular cross-sectional shape, extending away from base 114 to an apex disposed within opening 124. The apex may include a smaller cross-sectional width than a base of the teeth. In such a configuration, the sides of each of the teeth may extend at angles away from base 114. As shown in FIG. 5A, the angle between a side of a tooth and base 114 may be greater than 90 degrees. According to another aspect, each tooth may be disposed about base 114 approximately 90 degrees apart from an adjacent tooth. Indeed, as shown, one of the teeth may be disposed opposite to gap 120, while two of the teeth may be disposed opposite to each other. It should be appreciated, however, that the teeth may be disposed at any suitable orientation relative to one another and/or base 114. Spacing engaging elements 126 apart from each other (e.g., to create gaps between adjacent engaging elements 126), and/or using engaging elements terminating in apices, may reduce the size of the contact area between retainer device 112 and engagement device 128. Reducing the contact area may reduce friction between retainer device 112 and engagement device 128, which may facilitate inserting engagement device 128 into retainer device 112. As can be appreciated, the interior surfaces of the retainer device 112 may be formed without the use of teeth to provide, alternatively, a smooth continuous surface in place of the teeth 126, or to provide a series of smaller teeth 126.

Those of ordinary skill will readily recognize that base 114 may include a greater or lesser number of teeth disposed closer or farther, respectively, to one another. Furthermore, it is contemplated that each tooth may extend radially away from base 114 such that the apices of the teeth are positioned equidistantly about a center of opening 124 when, for example, the retainer device 112 is in a deflected or expanded state. Such positioning may allow the teeth to center engagement device 28 within opening 124. Moreover, retainer device 112 may be positioned along bore 20 of header 16, with engaging elements 126 extending into bore 20. In this manner, engaging elements 126 may center engagement device 28 within bore 20.

In order to facilitate movement between deflected/expanded and undeflected/contracted states, retainer device 112 may be formed of a flexible and/or elastic material, such as one or more metals, polymers, or combinations thereof. In some embodiments, retainer device 112 may be made of shape memory or superelastic materials including, but not limited to, nitinol or stainless steel, which may allow retainer device 112 to be deflected and/or expanded when stressed by a force, and return to its original shape when the force is removed. It is further contemplated that retainer device 112 may be made of or coated with an insulating or non-conductive material to ensure that electrical energy is not conducted through retainer device 112.

More specifically, retainer device 112 may be configured to flex into an expanded configuration when, for example, one or more opposing forces, identified by arrows 128 and 130 (FIG. 5B), is applied to retainer device 112. One or more opposing forces 128 and 130 may be applied against engaging elements 126 by engagement device 28. Additionally or alternatively, one or more of opposing forces 128 and 130 may be applied against ends 116 and 118 by an implement 132. FIG. 5B depicts aspects of an exemplary implement 132. Implement 132 may include a tapered portion 134 that may be brought into contact with ends 116 and 118 of retainer device 112 through, for example, recess 27 in header 16 (FIG. 2A). Septum 29 may be removed prior to the introduction of implement 132 into recess 27, or implement 132 may be used to penetrate septum 29 to gain entry into recess 27. As implement 132 is forced against ends 116 and 118 of retainer device 112, tapered portion 134 may force apart ends 116 and 118. One or more of forces 128 and 130 may cause base 114 to pivot, for example, at portions of base 114 on opposing sides of hub 122, and/or may cause expansion of a radius of curvature of base 114, to deflect and/or expand base 114 sufficiently to allow disengagement between the retainer device 26 and the corresponding surfaces of the engagement portion 28 to allow removal of the lead 14 from the bore 20.

In another exemplary embodiment, base 114 may not be deformed by one or more of forces 128 and 130, but rather, engaging elements 126 may be deformed. For example, engaging elements 126 may bend or pivot along an axial direction of opening 124 when engaged by the outer surface of engagement device 28. Additionally or alternatively, engaging elements 126 may be spring-loaded on base 114, such that engaging elements 126 may retract into recesses (not shown) on base 114 upon being engaged by the outer surface of engagement device 28. When one or more of forces 128 and 130 is removed, and/or when engagement device 28 is extracted from opening 124, base 114 and/or engaging elements 126 may be configured to return to their original states, bringing retainer device 112 to its undeflected and/or contracted state.

Engaging elements 126 may be made of a material having different characteristics than the material forming base 114. For example, engaging elements 126 may be more rigid than base 114, to avoid deforming engaging elements 126 and encourage deformation of base 114, or more flexible than base 114, such that deformation of base 114 may be avoided while deformation of engaging elements may be encouraged. Alternatively, all portions of the retainer device 112 may be made of the same material. In some embodiments, retainer device 112 may be made of a one-piece construction. In other embodiments, engaging elements 126 may be mechanically secured to base 114. Any suitable form of mechanical securement may be used, including selectively detachable forms of mechanical securement that may allow engaging elements 126 to be removably attached to base 114.

Turning to FIGS. 6A-6D, an exemplary engagement device 44 and an exemplary retainer device 112 are depicted at progressive stages of insertion of engagement device 44 into retainer device 112 during, for example, insertion of lead 14 into header 16. While the description below refers to interactions between specific types of engagement and retainer devices, the principles described below may be applicable to any of the exemplary engagement devices and exemplary retainer devices described in the present disclosure.

With reference to FIG. 6A, engagement device 44 is shown prior to coming into contact with retainer device 112. An arrow 136 in the drawing indicates the direction engagement device 44 may travel when being inserted into retainer device 112. As shown at the bottom of FIG. 6A, retainer device 112 may be in an undeflected and/or contracted state.

With reference now to FIG. 6B, engagement device 44 is shown with tapered portion 48 contacting retainer device 112, as a result of a proximal end of engagement device being inserted into opening 124 of retainer device 112. Tapered portion 48 may deflect and/or expand retainer device 112 by, for example, forcibly contacting engaging elements 126. The axial view of retainer device 112 in FIG. 6B shows that tapered portion 48 may cause base 114 to deflect and/or expand radially outwardly. The deflection and/or expansion may increase as engaging elements 126 slide up the positive-sloped surface of tapered portion 48. Arrows 138 and 140 indicate directions of movement of ends 116 and 118 of retainer device 112. One of ordinary skill would appreciate that implement 132 (FIG. 5B) may be used to help deflect and/or expand base 114 to make it easier to insert engagement device 44 into retainer device 112.

At the stage shown in FIG. 6C, tapered portion 48 of engagement device 44 has passed through opening 124 of retainer device 112, and engaging elements 126 have come into contact with cylindrical portion 50 of engagement device 44. Retainer device 112 may be at its most deflected and/or expanded state because cylindrical portion 50 may be the largest-diameter portion of engagement device 44. Cylindrical portion 50 may maintain retainer device 112 in this deflected and/or expanded state during further insertion of engagement device 44 into retainer device 112.

Next, as shown in FIG. 6D, engaging elements 126 may move out of contact with cylindrical portion 50 of engagement device 44 by moving distally past shoulder 52. In the absence of the deflecting and/or expanding force exerted on retainer device 112 by cylindrical portion 50, retainer device 112 may move toward a less deflected and/or contracted state. This movement is indicated by arrows 142 and 144 in the drawing, and may bring engaging elements 126 into contact with cylindrical portion 54 with sufficient force to produce audible and/or tactile feedback. The feedback may be in the form of a click, including a short, sharp sound and/or impact. The feedback may be heard or felt by the user, providing the user with an indication that engagement device 44 is secured to retainer device 112, and thus, lead 14 is secured within header 16. Additionally or alternatively, engaging elements 126 and cylindrical portion 54 may be magnetically attracted to each other to enhance mechanical engagement between engagement and retainer devices 44 and 112. The securement described above may be provided without the use of any set screws. Alternatively, the securement described above may be provided to reduce the number of set screws used to secure lead 14 to header 16. As illustrated in FIG. 6D, the inner surface of retainer device 112 may be configured to engage the bottom of the channel defined by surface 54. Alternatively, the inner surface of the retainer device 112 or the depth of the channel defined by surface 54 may be configured so that there is a floating engagement between the inner surface of the retainer device 112 and the surface 54, with the engagement primarily maintained by the interference provided by the side walls defining the channel or groove. As can be appreciated, this floating engagement (or the floating engagement between the exterior surfaces of the retainer device 112 and the interior walls defining the cavity 20a) may permit the lead 14 to rotate within the bore while maintaining electrical connections between the lead 14 and the header 16. This rotational freedom advantageously reduces stress that may be imparted to the lead or header when the lead is rotated relative to the IPG. It is believed that set screws that provide a fixed and non-rotational engagement between a lead and an IPG may not relieve such rotational stresses.

In some instances, the user may have reason to extract lead 14 from header 16. For example, the user may want to replace lead 14 with another lead to improve performance of IPG 12. The user may first extract engagement device 44 from retainer device 112 to extract lead 14 from header 16. The extraction of engagement device 44 from header 16 may be accomplished in a number of ways. In one exemplary embodiment, implement 132 may be used to exert an external deflecting force on retainer device 112 (FIG. 5B) to, for example, clear engaging elements 126 from a path of shoulder 52 of engagement device 44, thus allowing shoulder 52 to move distally relative to retainer device 112. Additionally or alternatively, implement 132 may be provided with a demagnetizing field to reduce any magnetic attraction between engagement device 44 and retainer device 112. Engagement device 44 then may be extracted from retainer device 112 by continuing to move distally relative to retainer device 112 until engagement and retainer devices 44 and 112 are separated. The progression of the extraction steps may, for example, be the opposite of the progression of the insertion steps in FIGS. 6A-6D.

Additionally or alternatively, in another exemplary embodiment, negative-sloped surfaces, like the ones on engagement devices 62, 70, 82, 92, and 104 (FIGS. 4B, 4C, 4E, 4G, and 4H), may deflect and/or expand retainer device 112 as the user exerts a distal pulling force on lead 14. Doing so may force engaging elements 126 and/or base 114 apart, facilitating further extraction of engagement devices 62, 70, 82, 92, and 104 from retainer device 112. One of ordinary skill would appreciate that any combination of the above-described extraction processes may be combined to bring about extraction of engagement devices 62, 70, 82, 92, and 104 from retainer device 112, and lead 14 from header 16.

Figure 7C:
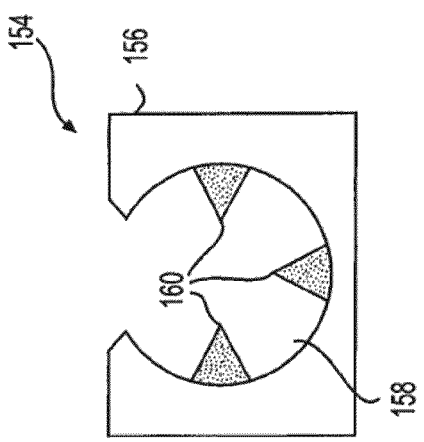
FIGS. 7A-7C are axial views of exemplary retainer devices, according to further aspects of the present disclosure.
Figure 7B:
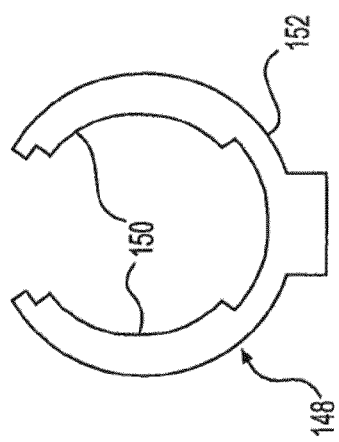
Figure 7A:
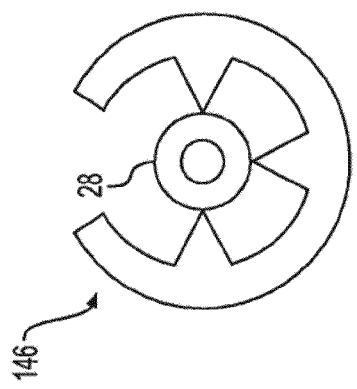

With reference to FIGS. 7A-7C, retainer device 26 may include one or more of the features described in connection with the exemplary embodiments illustrated in those figures. In one exemplary embodiment illustrated in FIG. 7A, a retainer device 146 may be similar to retainer device 112, except retainer device 146 may not include hub 122. In such an embodiment, retainer device 146 may be received in an annular recess or groove (not shown) surrounding bore 20 of header 16. Portions of axially-facing surfaces of retainer device 146 may engage portions of axially-facing surfaces of the annular recess or groove, which may limit or prevent movement of retainer device 146 relative to header 16 in a longitudinal direction of bore 20. However, retainer device 146 may have the ability to rotate within the annular recess, groove, or cavity 20a and/or about a central longitudinal axis of bore 20. Thus, retainer device 146 may secure engagement device 28 and lead 14 to header 16, while permitting lead 14 to rotate relative to header 16 and thereby prevent torsional stress from developing in lead 14 due to twisting of distal portions of lead 14. Retainer device 146 is shown in securing engagement with engagement device 28 in FIG. 7A.

In another exemplary embodiment illustrated in FIG. 7B, a retainer device 148 may be similar to retainer device 112 (FIG. 5A), except retainer device 148 may include engaging elements 150 rather than engaging elements 126. Though, engaging elements 150 may be, in some ways, functionally similar to engaging elements 126 (e.g., teeth) of FIG. 5A, engaging elements 150 may include a substantially differing geometric configuration. For example, as shown in FIG. 7B, each engaging element 150 may extend along an arc length of a base 152 that is larger than that of engaging elements 126. In addition, rather than extending away from base 152 to an apex, each engaging element 150 may define an elongated radial surface configured to engage engagement device 28. In such a configuration, side edges of engaging elements 150 may be disposed substantially perpendicularly to base 152. Though FIG. 7B depicts only two engaging elements 150, base 152 may include any suitable number of engaging elements 150. Arc lengths of engaging elements 150 may be modified to be shorter to fit additional engaging elements on base 152, and modified to be longer if fewer engaging elements are provided on base 152.

In yet another exemplary embodiment illustrated in FIG. 7C, an exemplary retainer device 154 may be similar to retainer device 112 (FIG. 5A), but may include a base 156 that differs from base 114. For example, base 156 may have a rectangular or rhombic configuration, or in the alternative, may have any other suitable polygonal configuration (and the cavity 20a may be similarly shaped). Base 156 may define a circular opening 158 that may extend axially through base 156. Engaging elements 160, similar to engaging elements 126, may extend from base 156 into opening 158. Retainer device 154 may or may not include hub 122 of FIG. 5A. Base 156 may be configured to be received in a corresponding opening, groove, or slot (not shown) provided in header 16. One or more sides, edges, or corners of base 156 may engage one or more surfaces of the corresponding opening, groove, or slot provided in header 16 to restrict relative movement (e.g., longitudinal, translational, and/or rotational movement) between base 156 and header 16. In some embodiments, surfaces of header 16 may contact at least three sides of base 156.

With reference to FIGS. 2A-2B, regardless of the specific configuration used, retainer device 26 may be configured to secure lead 14 within header 16 by limiting or preventing longitudinal movement of engagement device 28 relative to retainer device 26. It should be appreciated that each of the various retainer device configurations described above (FIGS. 5A and 7A-7C) may permit rotational movement of lead 14 and engagement device 28 relative to header 16 and retainer device 26 to, for example, reduce or eliminate torsional stress on lead 14. Moreover, use of retainer device 26 to secure engagement device 28 may eliminate the need for using set screws to secure lead 14 to header 16, or at least reduce the number of set screws used to secure lead 14 to header 16.

According to another contemplated aspect, the positioning of: (1) tapering portions, cylindrical portions, shoulders, and/or recessed portions or grooves of the disclosed exemplary engagement devices, and (2) engaging elements of the disclosed exemplary retainer devices may be reversed. For example, engaging elements may be positioned on an outer surface of an engagement device, and may extend radially outwardly from the outer surface. Tapering portions, cylindrical portions, shoulders, and/or recessed portions or grooves, for engaging/receiving engaging elements, may be provided on an inner surface of a retainer device. In such an embodiment, the engagement device and/or engaging elements may be moved into a deflected and/or contracted state during insertion of the engagement device into the retainer device, and may move to a less deflected, undeflected, and/or expanded state and into one of the recessed portions or grooves, to secure the engagement and retainer devices. While the positioning of the various aspects may be reversed, the processes of insertion, securement, and extraction may remain the substantially same.

Figure 8:
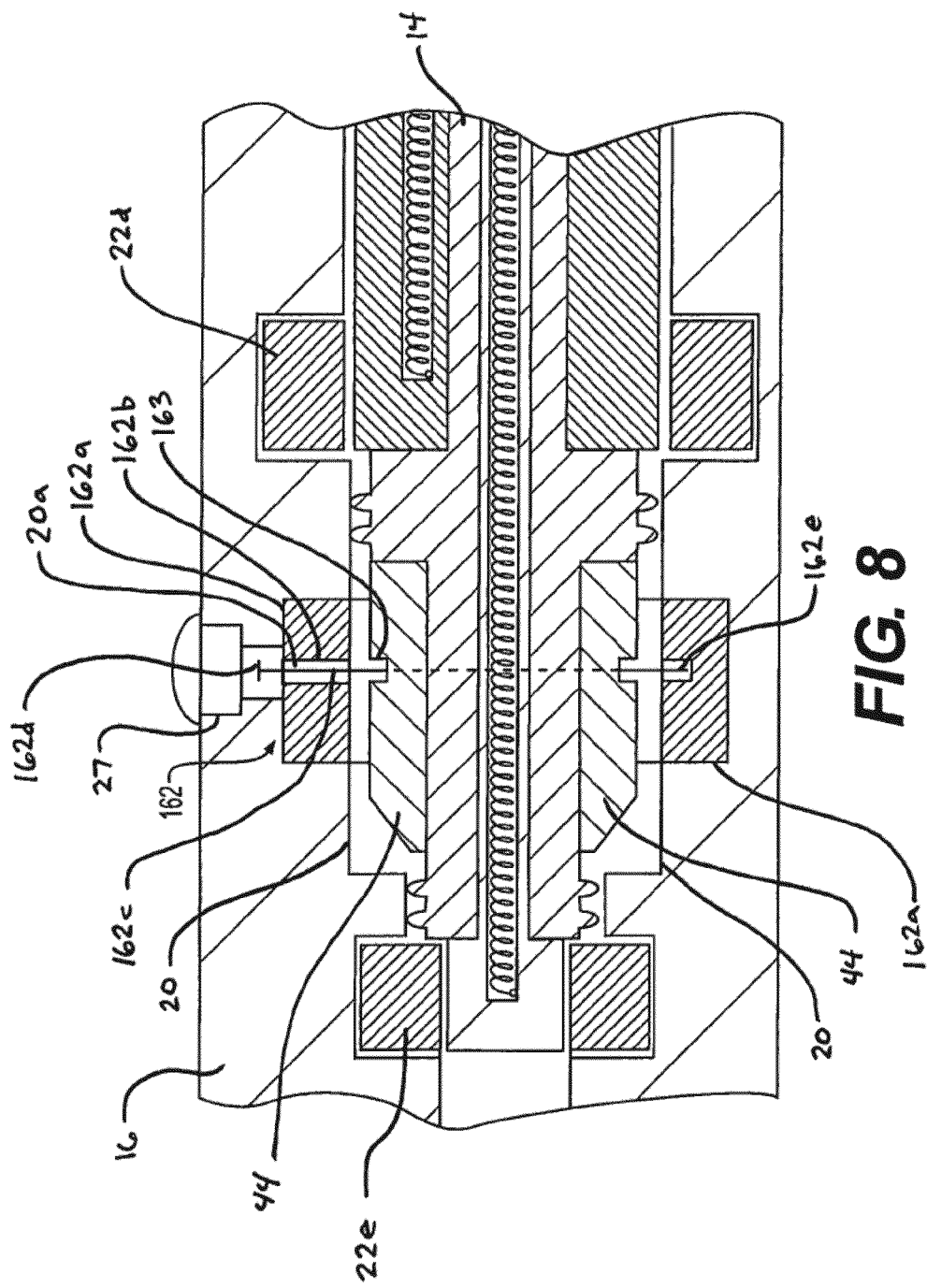
FIG. 8 is a cross-sectional view of the IPG and lead of FIG. 1, showing an enlarged view of the interior region of the header of the IPG, including an exemplary engagement device and another exemplary retainer device, according to an aspect of the present disclosure.

With reference now to FIG. 8, illustrated is a cross-sectional view of another embodiment similar to the embodiment illustrated in FIG. 3 (some similar components are not relabeled in FIG. 8). Some differences presented in the FIG. 8 embodiment include the introduction of a retaining mechanism 162. As illustrated in FIG. 8, the retaining mechanism 162 may include a ring 162a that replaces a portion of header interior surface that defines bore 20. The ring 162a may include an interior surface that abuts the header interior surfaces defining the remainder of bore 20 and may include additional interior surfaces that define a cavity 162b that replaces the cavity 20a illustrated in FIG. 2A, for example. The retaining mechanism 162 may also replace the circular or arcuate retainer device 26 (as illustrated in FIGS. 5A-7C, for example) with a flexible strand, fiber, elongated member, or wire 162c that may extend from one side of the ring 162a to an opposing side of the ring 162a to dispose the wire 162c across the bore 20. The wire 162c may include an actuator end 162d that can be accessed via the passage 27 so that the actuator end 162d may be pulled, depressed, rotated, or twisted to impart an alternate shape to the wire 162c as it extends through the bore 20, to allow the wire 162c to assume a first shape having a relaxed orientation that occludes a portion of the bore 20 (or that inhibits the ingress or egress of the lead from the bore 20) and a second shape having a deformed orientation that does not occlude the bore 20 or prevent the ingress or egress of the lead 14 from the bore 20. The wire 162c may also have an opposing end 162e that may be fixed to the ring 162a and/or supported in a sliding, rotating, or high-friction engagement that may be configured to oppose any forces imparted to the wire 162c at the actuator end 162d. As illustrated, the wire 162c may be disposed to pass across the bore 20 between the actuator end 162d and the opposing end 162e, and the wire 162c may be sized and configured to allow movement within the bore 20 in a direction that is orthogonal to the axis of the bore so as to move the portion of the wire 162c extending through the bore 20 off to a side of the bore 20 to permit the movement of the lead 14 and the engagement device 44 (or any of the other disclosed engagement devices) past the wire 162c to dispose a portion of the wire 162c in a channel 163 defined by the exterior surface of the engagement device 44 to secure lead 14 within bore 20 of header 16 (as also illustrated in FIGS. 2A-2B). Retaining mechanism 162 also may be electrically isolated from one or more portions of header 16, and/or from one or more portions of lead 14. For example, retaining mechanism 162 may be electrically isolated from electrical contacts 22d and 22e of header 16, and/or from electrical contacts or electrodes 40 and 42 on lead 14 (FIG. 3). Further, retaining mechanism 162 may include any feature or combination of the features described in connection with the exemplary embodiments discussed below in more detail. As can be appreciated, the retaining mechanism 162 may be configured without the use of ring 162a, using instead the structure of the bore 20 and cavity 20a illustrated in, for example, FIGS. 2A-2B. As can also be appreciated, for clarity the thickness of the header 16 illustrated in FIG. 8 has been reduced to better show the interaction of components internal to the header. The length of wire 162c may be significantly longer than the length shown in FIG. 8, and the movement of the actuator end 162d within the passage 27 and the movement or distending of the wire 162c within the bore may be more pronounced than shown in FIG. 8.

Figure 9A:
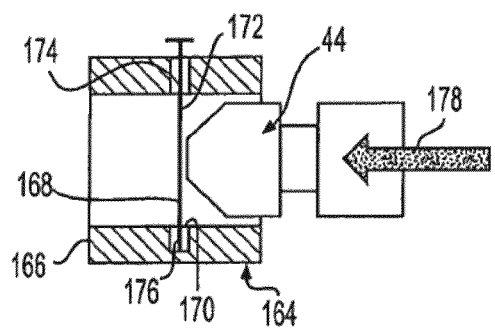
FIGS. 9A-9F illustrate axial and side views of an exemplary engagement device being inserted into an exemplary retainer device, according to an aspect of the present disclosure.
Figure 9B:
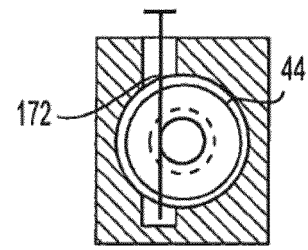

FIGS. 9A-9F illustrate a progression of the engagement portion 44 of the lead 14 as it is inserted into the portion of the bore 20 defined by the retaining mechanism 162, which involves the deflection of the 162c to disposed the wire 162c in the channel 163 of the engagement portion 44. With specific reference to FIGS. 9A and 9B, retaining mechanism 164 may include a base (or ring) 166 (shown with a square outer surface instead of the circular outer surface shown in FIG. 8) and an engaging element (or wire) 168 coupled to base 166. Base 166 may include a bore 170, and engaging element 168 may be secured to base 166 such that engaging element 168 may extend across bore 170. Engaging element 168 may, for example, follow a chord or secant line intersecting two points along the surface of bore 170 as illustrated in FIG. 9B, which shows an end view of the FIG. 9A structures from a proximal end of the bore 20. Base 166 may be fixedly secured within header 16 such that bore 170 of base 166 may be aligned with bore 20 of header 16 (FIGS. 2A-2B). In an alternative embodiment, base 166 of retaining mechanism 164 may be omitted. Instead, retaining mechanism 164 solely may include engaging element 168 disposed within and extending across bore 20 of header 16.

Engaging element 168 may include at least one flexible elongate member, such as, for example, a wire member 172. Wire member 172 may extend across bore 170 such that wire member 172 may be offset from a center of bore 170. Wire member 172 may be made of any suitable material, such as, for example, shape memory or superelastic materials including, but not limited to, nitinol or stainless steel. Wire member 172 may be movable between a deflected or relaxed state, for facilitating insertion and/or extraction of engagement device 44, and an undeflected or taut state, for engaging engagement device 44. Wire member 172 may be moved to the deflected state by engagement device 44 when lead 14 is inserted into header 16, and the outer surface of engagement device 44 is forced against wire member 172. Additionally or alternatively, an end portion 174 of wire member 172 may extend beyond an outer surface of base 166 into, for example, recess 27 in header 16 (FIGS. 2A-2B), so that end portion 174 may be pressed or otherwise actuated (for example, by implement 132) to deflect and/or relax wire member 172 to move wire member 172 out of plane. The end portion 174 also may be pushed, pulled, rotated, or twisted to cause a shape change in the portion of wire member 172 extending through the bore 170. In another embodiment, end portion 174 may extend beyond an outer surface of header 16, where it may be pressed or otherwise actuated by implement 132 or manually, and the actuation of the end portion 174 may be achieved without breaching the seal provided at the end of passage 27 by plug 20c. Another opposing end portion 176 of wire member 172 may be secured to a wall of bore 170 or base 166, may be secured in a rotational engagement allowing the wire member 172 to rotate, and/or may be disposed in a sliding engagement allowing the wire member 172 to disengage with the wall of bore 170 or to move in a direction transverse an axis of the bore 170 without fully disengaging from the wall of the bore 170. Alternatively, end portion 176, like end portion 174, may extend beyond an outer surface of base 166 and/or header 16, so that end portion 176 may be actuated to manipulate wire member 172 in a manner similar to the end portion 174.

Figure 9C:
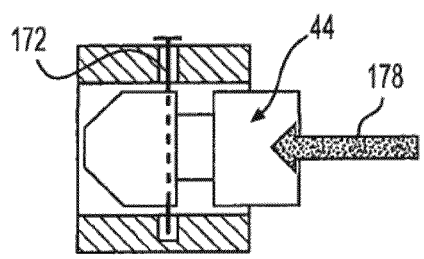
Figure 9D:
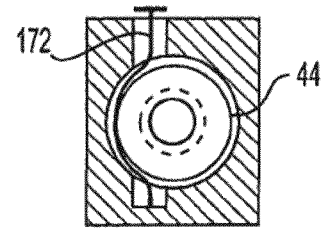
Figure 9E:
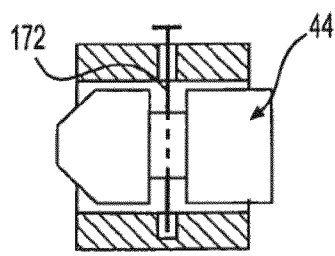
Figure 9F:
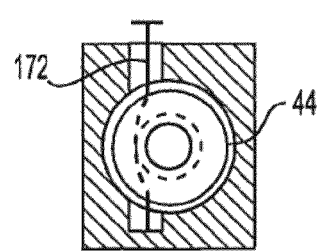

With reference again to FIGS. 9A-9F, engagement device 44 and retaining mechanism 164 are depicted at progressive stages of insertion of engagement device 44 into retaining mechanism 164 during, for example, insertion of lead 14 into header 16. In particular, FIGS. 9A and 9B show side and front views of engagement device 44 moving in a proximal direction, identified by an arrow 178, into bore 170, but not yet to the point of making contact with wire member 172. Next, FIGS. 9C and 9D show side and front views of engagement device 44 in contact with wire member 172. In going from the state shown in FIGS. 9A and 9B to the state shown in FIGS. 9C and 9D, tapered portion 48 of engagement device 44 may deflect wire member 172 into a bent or deflected configuration, facilitating further insertion of engagement device 44. Cylindrical portion 50 of engagement device 44 may maintain this deflection during continued insertion of engagement device 44. Then, as seen in FIGS. 9E and 9F, engagement device 44 is secured to retaining mechanism 164 with wire member 172 seated in the recessed portion or groove defined by shoulder 52, cylindrical portion 54, and shoulder 56 of engagement device 44 (FIG. 4A). Upon moving distally past shoulder 52, wire member 172 may return to a less deflected or undeflected state, and/or may become more taut, such that contact between wire member 172 and cylindrical portion 54 may be made with sufficient force to produce audible and/or tactile feedback. One of ordinary skill will appreciate that a distance between shoulders 52 and 56 of engagement device 44 may be equal to a width of wire member 172, for enhanced securement. Once secured, engagement device 44 may be fixed relative to retaining mechanism 164, in that longitudinal movement of one relative to the other may be inhibited or prevented. However, rotational movement of one of engagement device 44 and retaining mechanism 164 relative to the other may be permitted to help alleviate any torsional stress in lead 14. Extraction of engagement device 44 from retaining mechanism 164 may be accomplished through the performance of steps similar to the insertion steps, but in reverse order. In some embodiments, however, wire member 172 may be deflected by actuating end portion 174, to facilitate extraction of engagement device 44.

FIGS. 10A-10C illustrate a plan or cross-sectional views of various embodiments that correspond to the embodiments illustrated in FIGS. 9A-9F. FIGS. 10A-10C depict end views of engagement device 44 and a retaining mechanism 180 at progressive stages of insertion of engagement device 44 into retaining mechanism 180. Retaining mechanism 180 may be similar to retaining mechanism 164, except retaining mechanism 180 may substitute the wire member 182 with a looped wire member 184 having a loop sized and configured to disposed a portion of the loop in the channel or groove of the engagement device to secure the lead 14 in the bore 20. Loop 184 may be rotated, compressed, deflected, and/or expanded in diameter to facilitate insertion and extraction of engagement device 44 into and out of retaining mechanism 180. Loop 184 may return to an undeflected, contracted, and/or reduced diameter state to secure engagement device 44 in retaining mechanism 180 when a portion of the wire member is disposed in the channel or groove of the engagement device 44. FIG. 10A depicts engagement device 44 prior to insertion with the loop 184 having a minimum diameter that is sized and position to receive the initial proximal surface of the engagement device, which may have a chamfer to facilitate alignment of components as illustrates in FIGS. 9A and 9C. FIG. 10B depicts engagement device 44 during insertion through the loop 184, with engagement device 44 deflecting and/or expanding the diameter of loop 184 to a greater diameter (which in turn draws inward at least one of the ends of the wire member 182). FIG. 10C depicts loop 184 after returning to a reduced diameter state with the wire member 182 and loop 184 disposed in the channel or groove of the engagement device 44.

FIGS. 11A and 11B illustrate an alternative embodiment of a wire member 186 shown without the surfaces of the bore 20 for clarity. Closed looped wire member 186 may, for example, replace looped wire member 184 in retaining mechanism 180. Wire member 186 may include an inner loop 188 and an outer loop 190, one or more of which may have a cardioid shape, and may be configured so that the inner loop 188 provide a smaller inner dimension than a corresponding inner dimension of the outer loop 190 when the wire member 184 is in a relaxed state defined by the dimensions of the bore. Inner loop 188 may be moved into a deflected and/or expanded state (FIG. 11B) through forceful engagement with the insertion of the engagement device 44, and/or the application of an external deflecting and/or expanding force applied in the direction of an arrow 187 by implement 132 or manually. As can be appreciated, the expansion of the inner loop 188 causes the reduction of the outer loop 190 as the two loops adjust to come to share a same or similar inner dimension that is greater than the inner dimension presented by the inner loop 188 when in the relaxed state. After full insertion of the engagement device and the alignment of the channel with the inner and outer loops 188, 190, the Inner loop 188 may move back toward an relaxed, undeflected, and/or contracted state (similar to FIG. 11A) to secure engagement device 44 by the insertion of the inner loop 188 within the channel of the engagement device.

With reference to FIGS. 12A-12C, engagement device 44 and a retaining mechanism 192 are depicted at progressive stages of insertion of engagement device 44 into retaining mechanism 192, with the end views presented in FIGS. 12A-12C corresponding to FIGS. 10A-10C (or FIGS. 9A, 9C, and 9E) respectively. Retaining mechanism 192 may function similarly to retaining mechanism 164 or retaining mechanism 180, except that retaining mechanism 192 may include a wire mesh or rhombus 193 that replaces the wire 172 or the loop 184. In one exemplary embodiment, wire mesh 193 may be formed by a plurality of interconnected wire segments 196, 198, 200, and 202 and may be in the form of a rhombus. Wire segments 196, 198, 200, and 202 may be separate segments joined together, or may be sections of a continuous length of wire. Wire segments 196, 198, 200, and 202 may be arranged in a rhombic shape that can be deformed into a square shape. While four wire segments 196, 198, 200, and 202 are depicted, this number of wire segments is exemplary and not necessarily limiting. Any number of wire segments may be used. For example, wire mesh 193 may include a curtain of interwoven wire segments (not shown) with a rhombic or polygonal cutout in a central portion of the curtain. Segments of the curtain around the cutout may function similarly to wire segments 196, 198, 200, and 202.

Portions of each of wire segments 196, 198, 200, and 202 may extend across a bore 203 to engage the outer surface of engagement device 44 when engagement device 44 is within bore 203. Wire mesh 193 may have a deflected and/or expanded state (FIG. 12B). In moving to the expanded state, the length of one or more of the distances defined between wire segments 196, 198, 200, and 202, may change, and/or the angles defined between the wire segments 196, 198, 200, and 202 may change, to create a bigger opening in a central portion of wire mesh 193. Wire mesh 193 may be moved to the expanded state by engagement device 44, implement 132, and/or manually. Wire mesh 193 may return toward an undeflected and/or contracted state (FIG. 12C) to secure engagement device 44. In returning toward the undeflected and/or contracted state, the orientations of wire segments 196, 198, 200, and 202 may change to reduce the size of the opening in the central portion of wire mesh 193.

With reference to FIGS. 13A-13C, engagement device 104 and a retaining mechanism 204 are depicted at progressive stages of insertion of engagement device 104 into retaining mechanism 204. FIG. 13A depicts engagement device 104 prior to insertion, FIG. 13B depicts engagement device 104 during insertion, and FIG. 13C depicts engagement device 104 when secured with retaining mechanism 204. Retaining mechanism 204 may include a wire member 206 similar to wire member 172 (FIGS. 9A-9F). Retaining mechanism 204 may differ in that it may also include at least one additional wire member 208 similar to wire member 172. In one exemplary embodiment, wire members 206 and 208 may be spaced apart in a longitudinal direction along a bore 209. Wire members 206 and 208 may extend along a same side of bore 209, or may extend along opposing sides of bore 209 as shown in FIGS. 13A-13C. In some embodiments, wire members 206 and 208 may be parallel. In other embodiments, wire members 206 and 208 may be angled relative to each other (i.e., non-parallel). In another embodiment, wire members 206 and 208 may be coplanar. In still another embodiment, wire members 206 and 208 may lie in intersecting planes. Additionally or alternatively, more than two wire members 206 and 208 may be provided, each of the wire members being configured to contact a different portion of engagement device 104.

During insertion of engagement device 104 into retaining mechanism 204, engagement device 104 may engage wire member 208 before engaging wire member 206. At that point, engagement device 104 may be only partially secured to retaining mechanism 204. When continued insertion of engagement device 104 brings wire member 206 to the proximal end of cylindrical portion 110 of engagement device 104 (adjacent tapered portion 106), and wire member 208 to the distal end of cylindrical portion 110 (adjacent tapered portion 108), engagement device 104 may be fully secured to retaining mechanism 204.

Figure 14C:
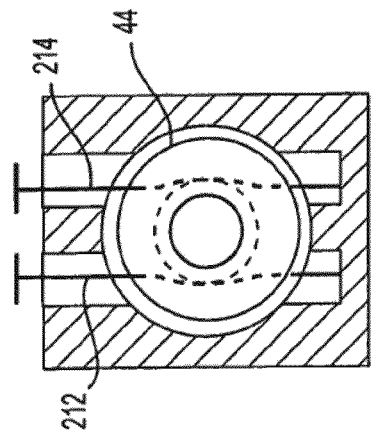
FIGS. 14A-14C illustrate axial views of an exemplary engagement device being inserted into another exemplary retainer device, according to an aspect of the present disclosure.
Figure 14B:
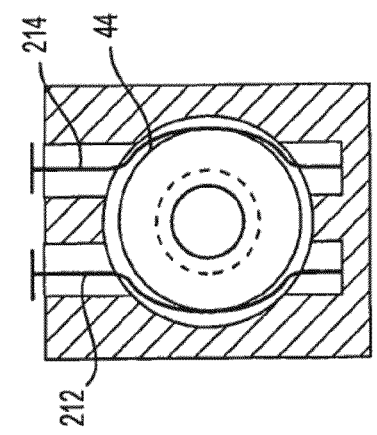
Figure 14A:
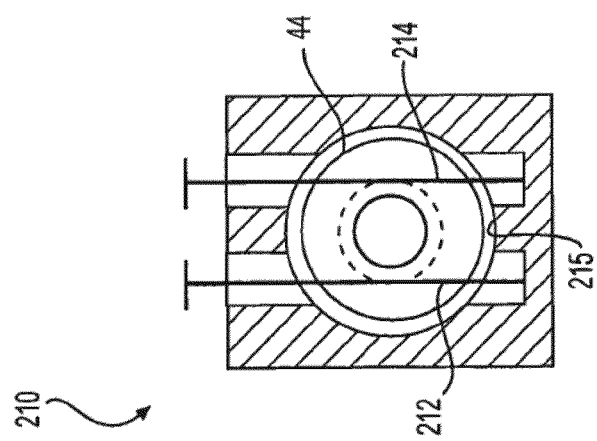

With reference to FIGS. 14A-14C, engagement device 44 and a retaining mechanism 210 are depicted at progressive stages of insertion of engagement device 44 into retaining mechanism 210. FIG. 14A depicts a front view of engagement device 44 prior to insertion, FIG. 14B depicts a front view of engagement device 44 during insertion, and FIG. 14C depicts a front view of engagement device 44 after having been secured with retaining mechanism 210. Retaining mechanism 210 may include a wire member 212 similar to wire member 172 (FIGS. 9A-9F). Like retaining mechanism 204, retaining mechanism 210 may also include at least one additional wire member 214, also similar to wire member 172. However, wire members 212 and 214 may be positioned at the same longitudinal position along a bore 215, along opposing sides of bore 215. In some embodiments, wire members 212 and 214 may be parallel. In other embodiments, wire members 212 and 214 may be angled relative to each other (i.e., non-parallel). Additionally or alternatively, more than two wire members 212 and 214 may be provided, each of the wire members being configured to contact a different portion of engagement device 44.

During insertion of engagement device 44 into retaining mechanism 210, engagement device 44 may engage wire members 212 and 214 simultaneously, with wire members 212 and 214 acting on opposing surfaces of engagement device 44 to secure engagement device 44 in retaining mechanism 210. In one exemplary embodiment, each of wire members 206 and 208 (FIGS. 13A-13C) may be replaced with wire members 212 and 214, for added securement. In another exemplary embodiment, wire members 206 and 208 may include any of wire members 172, 182, 186, 212, and 214, or wire mesh 194.

Figure 15:
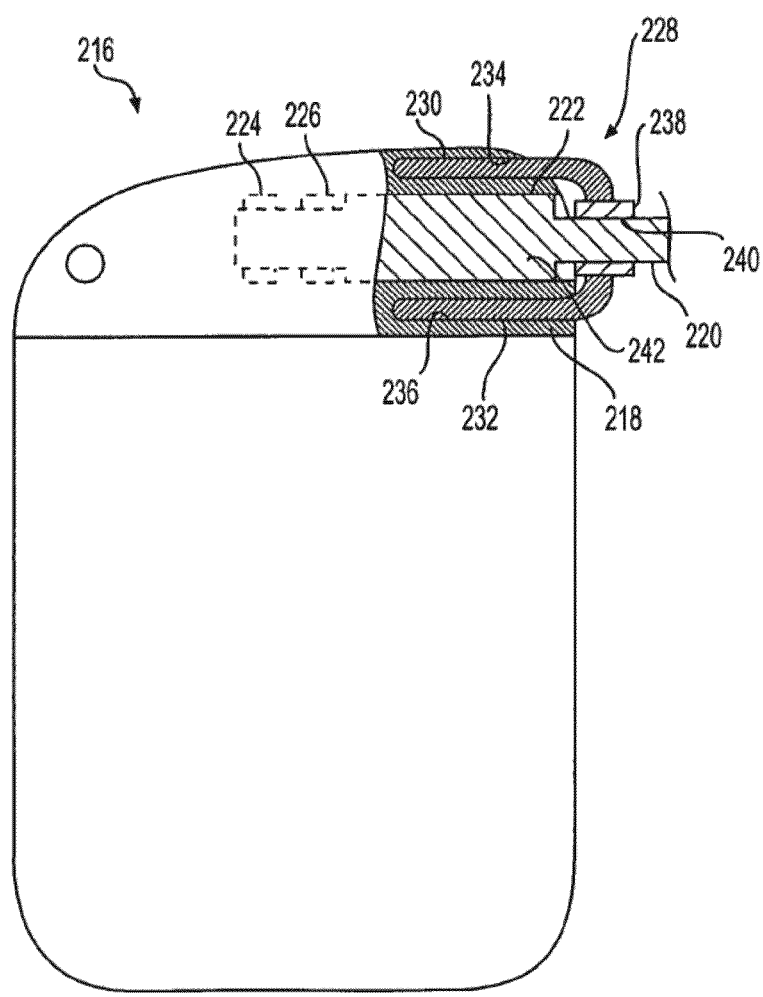
FIG. 15 illustrates a partial section view of portions of an exemplary IPG and lead, showing an interior region of a header of the IPG, according to an aspect of the present disclosure.

FIG. 15 illustrates an IPG 216 having a header 218, and a lead 220 inserted into header 218. Header 218 may include a bore 222, and first and second electrical device contacts 224 and 226 around bore 22 for receiving lead 220. Lead 220 may include one or more electrical contacts/electrodes (not shown), similar to electrical contacts/electrodes 40 and 42 (FIG. 3), configured to make contact with electrical device contacts 224 and 226. A engagement device 228 may be coupled to header 218, for securing and/or supporting lead 220 relative to header 218. Engagement device 228 may include one or more prongs 230 and 232. Each of prongs 230 and 232 may be inserted into one of recesses 234 and 236 in header 218. Once inserted, prongs 230 and 232 may be secured or retained in recesses 234 and 236 by frictional engagement, use of adhesives, and/or any other suitable form of attachment. In this embodiment, the portion of header 218 may act as a retainer device for engaging and securing engagement device 228. Engagement device 228 may be electrically isolated from electrical contacts 224 and 226 of 218, and/or from electrical contacts or electrodes (not shown) on lead 220.

Engagement device 228 may also include a ring 238, from which prongs 230 and 232 may extend. Ring 238 may be cylindrical in shape, with a bore 240 configured to receive a portion of lead 220. Portions of lead 220 may be slidable through and/or rotatable within bore 240. Prongs 230 and 232 may be provided in any suitable orientation around ring 238. For example, prongs 230 and 232 may be symmetrically or asymmetrically arranged around the ring 238, depending on the location of recesses 234 and 236 on header 218. It should also be understood that prongs 230 and 232 may have any size or shape suitable for securing ring 238 and lead 220 to header 218. It should also be understood that there may be more than two prongs 230 and 232 for securing and/or supporting purposes.

Still referring to FIG. 15, lead 220 may include an enlarged portion 242. Enlarged portion 242 may be useful for helping to secure lead 220 to header 218. For example, enlarged portion 242 may have a width greater than a width of bore 240 of ring 238. The distal end of enlarged portion 242 may abut the proximal end of ring 238, preventing extraction of enlarged portion 242 distally through ring 238. In one example, ring 238 may be flush with the outer surface of header 218 to keep lead 220 in place.

In use, engagement device 228 may be positioned on a proximal portion of lead 220. Lead 220 may be inserted into header 218, and engagement device 228 may slide over lead 220 toward header 218. Prongs 230 and 232 may enter recesses 234 and 236, securing engagement device 228 to header 218. Ring 238 may abut enlarged portion 242 of lead 220, limiting or preventing extraction of lead 220 from header 218. Alternatively, engagement device 228 and lead 220 may be coupled to header 218 at the same time. In other embodiments, engagement device 228 may be formed integrally with lead 220.

With reference to FIGS. 16A and 16B, alternative embodiments of headers 254 and 256 are depicted, each header 254 and 256 being configured to receive prongs 230 and 232 of engagement device 228. For example, header 254 (FIG. 16A), may include recesses 248 and 250, one on each side of a lead bore 252, for receiving prongs 230 and 232. Recesses 248 and 250 and bore 252 may be aligned along a first axis. With header 246 (FIG. 16B), recesses 254 and 256 (for receiving prongs 230 and 232) and a lead bore 258, may be aligned along a second axis angled (e.g., perpendicular) relative to the first axis. Other configurations of headers 244 and 246 are also contemplated, including embodiments where the recesses for prongs 230 and 232 may be arranged asymmetrically about a lead bore. In another contemplated embodiment, more than two recesses may be provided if more than two prongs are provided on an engagement device. Similarly, a single recess may be provided if a single prong is provided on an engagement device.

With reference now to FIGS. 17A and 17B, an engagement device 260 is depicted for coupling lead 220 to a header 262. Engagement device 260 may be similar to engagement device 228, except engagement device 260 may include protrusions 264 and 266 on prongs 268 and 270, respectively. Header 262 may be similar to header 218, except header 262 may include openings 272 and 274 configured to receive protrusions 264 and 266, respectively. During insertion of prongs 268 and 270 into recesses 276 and 278, prongs 268 and 270 and/or protrusions 264 and 266 may be deformed to facilitate insertion of prongs 268 and 270 into recesses 276 and 278. For example, one or more portion of prongs 268 and 270 and/or protrusions 264 and 266 may be deflected inwardly. When protrusions 264 and 266 reach openings 272 and 274, prongs 268 and 270 and/or protrusions 264 and 266 may return their undeflected states, causing protrusions 264 and 266 to enter openings 272 and 274. In one embodiment, protrusions 264 and 266 and openings 272 and 274 may form a snap-fit engagement mechanism. Put another way, the portion of header 262 that includes recesses 276 and 278, and openings 272 and 274, may act as a retainer device for engaging and securing engagement device 260.

According to an aspect of the present disclosure, when protrusions 264 and 266 enter openings 272 and 274, prongs 268 and 270 may move rapidly from their deflected states to their undeflected states. Portions of prongs 268 and 270 may come into contact recesses 276 and 278, producing audible and/or tactile feedback experienced by the user. According to yet another aspect, the positioning of protrusions 264 and 266 and openings 272 and 274 may be reversed. For example, protrusions 264 and 266 may be provided on header 262, while openings 272 and 274 (or recesses) may be provided on prongs 268 and 270.

A ring 280 of engagement device 260, which may be similar to ring 238 of engagement device 228, may include a bore 282 for receiving and supporting lead 220, and may keep lead 220 inserted in header 262 by engaging enlarged portion 242 of lead 220. In order to extract engagement device 260 from header 262, protrusions 264 and 266 may be pressed inwards to move them back out of openings 272 and 274, allowing engagement device 260 to be pulled away from header 262, after which, clearing the way for lead 220 to be extracted from header 262.

Turning to FIGS. 18A, 18B, and 19A, exemplary embodiments of retainer clips for positioning a lead 284 are illustrated. With specific reference to FIG. 18A, a portion of lead 284 may be looped backward or otherwise bent to have a fixed radius, such that the portion of lead 284 may be U-shaped. A retainer clip 286 may be provided on lead 284 to maintain lead 284 in the U-shaped configuration. Retainer clip 286 may include a bore 288 and a recess 290, separated by a central body portion 292 (FIG. 18B). Bore 288 and recess 290 may extend along opposing sides of retainer clip 286, with bore 288 being configured to receive one leg of the U-shaped portion of lead 284, and recess 290 being configured to the other leg of the U-shaped portion of lead 284. Walls of retainer clip 286 around recess 290 may define a gap 291 and may be deflectable such that they may form a snap-fit connection for receiving lead 284. By maintaining a fixed radius or U-shape in lead 284, excessive bending of lead 284 that could result in damaging lead 284 may be avoided.

FIG. 19 shows another exemplary retainer clip 294 configured to maintain a fixed radius or U-shape in lead 284. Retainer clip 294 may be similar to retainer clip 286, except retainer clip 294 may include a curved central body portion 296. Central body portion 296 may have a concave side and a convex side. The concave side may be adjacent to, or in contact with, the U-shaped portion of lead 284, giving central body portion 296 the ability to provide additional support to lead 284 for maintaining the fixed radius or U-shape, and preventing excessive bending.

Figures 20A, 20B, 21:
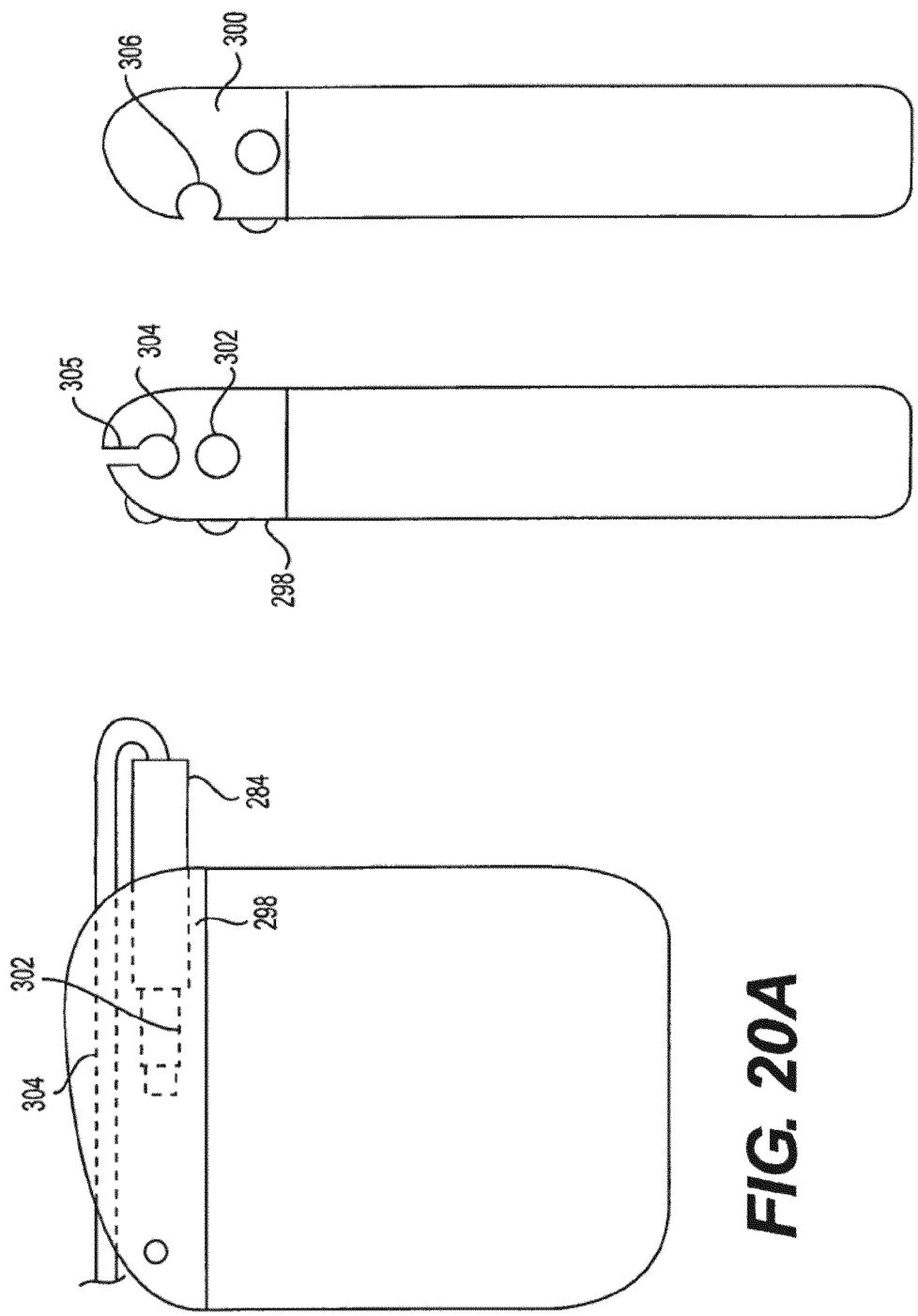
FIGS. 20A-20B depict a front view of an exemplary IPG and lead, and an end view of an exemplary header, according to further aspects of the present disclosure.
FIG. 21 shows an end view of a portion of an exemplary IPG header, according to another aspect of the present disclosure.

With reference to FIGS. 20A, 20B, and 21, headers 298 and 300 are depicted, with each of headers 298 and 300 being configured to maintain a fixed radius or U-shape in lead 284, without the use of separate fasteners. For example, FIGS. 20A and 20B show header 298 having a bore 302 configured to receive the proximal end portion of lead 284, and a recess 304 configured to receive a more distal portion of lead 284. In use, the proximal end portion of lead 284 may be inserted into bore 302, while the more distal portion of lead 284 may be looped backward or otherwise bent to create the fixed radius or U-shape, and then secured within an elongate recess 304 extending along, for example, a top edge portion of header 298. Walls of header 298 around recess 304 may define a gap 305 and may be deflectable such that they may form a snap-fit connection for receiving lead 284. With specific reference to FIG. 21, another exemplary header 300 is shown. Header 300 may be similar to header 298, except header 300 may include a recess 306 extending along a side face (e.g., front or back) of header 300 for receiving lead 284.

Figure 22A:
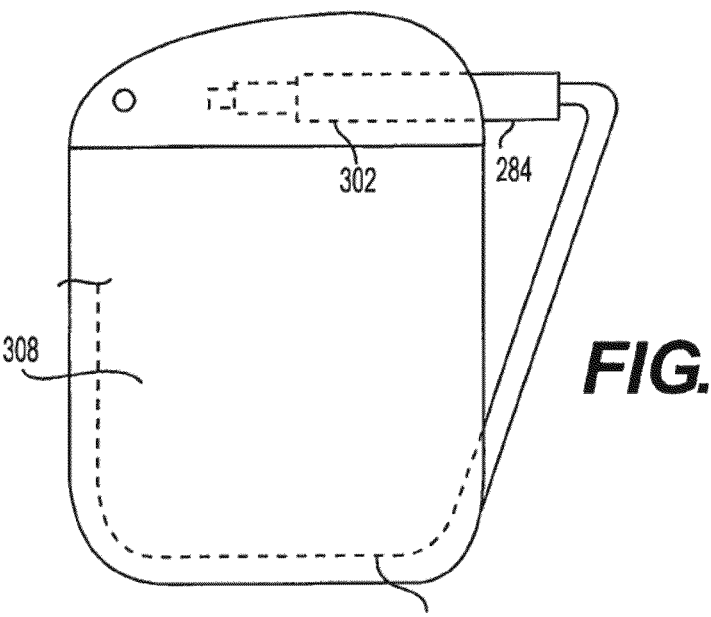
FIGS. 22A-22B illustrate a front view of an exemplary IPG and lead, and a bottom view of the IPG, according to a further aspect of the present disclosure.
Figure 22B:
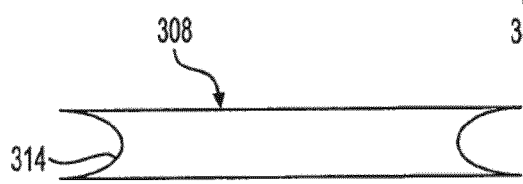
Figure 23:
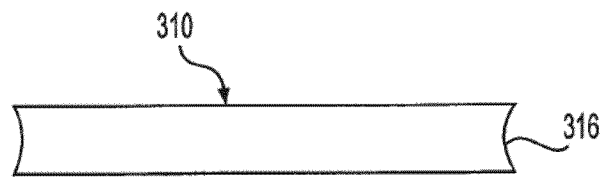
FIG. 23 illustrates a bottom view of another exemplary IPG, according to another aspect of the present disclosure.

With reference to FIGS. 22A, 22B, and 23, IPG enclosures 308 and 310 are depicted, with each of enclosures 308 and 310 being configured to receive a portion of lead 284. For example, FIGS. 22A and 22B show lead 284 extending away from header 312, and being wrapped around a bottom edge of enclosure 308. The edge of enclosure 308 may include a groove or recess 314 configured to receive lead 284, such that lead 284 is flush with the edge of enclosure 308, or recessed within the edge of enclosure 308. This arrangement may allow lead 284 to be taken up by being wrapped around enclosure 308, and/or may give lead a fixed radius or U-shape. FIG. 23 shows enclosure 310 having a recess 316 similar to recess 314, but with a shallower depth. A portion of lead 284 may be received in recess 316, while a parallel portion of lead 284 may protrude from recess 316 and from the edge of enclosure 310.

Figure 24:
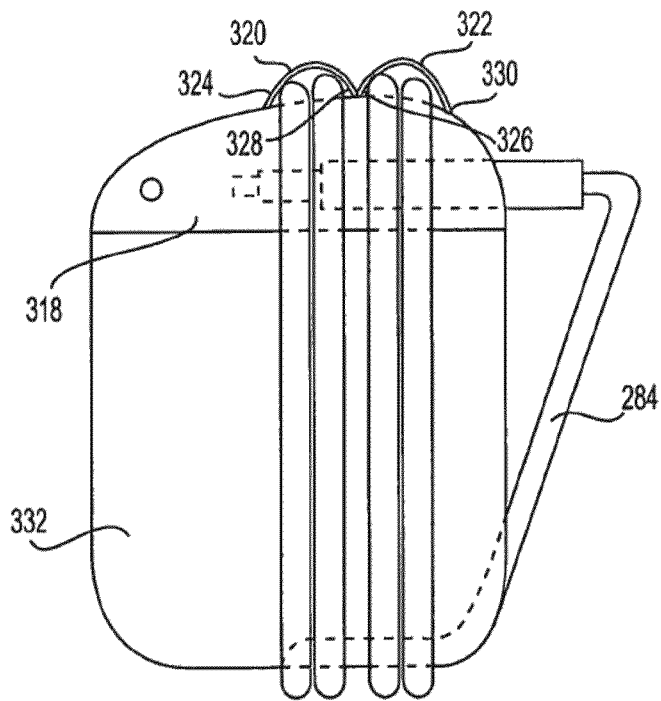
FIG. 24 illustrates a front view of an exemplary IPG and lead, according to another aspect of the present disclosure.

With reference to FIG. 24, a header 318 is depicted with one or more flaps 320 and 322 on one of its outer surfaces. Flaps 320 and 322 may be positioned at an edge portion (e.g., top) of header 318. In one embodiment, flaps 320 and 322 may include fixed ends 324 and 326 and free ends 328 and 330. Flaps 320 and 322 may pivot about their fixed ends 324 and 326, with their fixed ends 324 and 326 operating as living hinges. Flaps 320 and 322 may be pivoted away from the edge portion of header 318 to define a space between flaps 320 and 322 and header 318 for securing a portion of lead 284. With flaps 320 and 322 pivoted away from the surface of header 318, the user may wrap one or more turns of lead 284 around header 318 and an enclosure 332. Flaps 320 and 322 may be pivoted back toward the surface of header 318 to help secure the wrapped turn(s) of lead 284. Alternatively, each of flaps 320 and 322 may have two fixed ends, and lead 284 may be threaded between flaps 320 and 322 and header 318 as lead 284 is wrapped around header 318. In one exemplary embodiment, flaps 320 and 322 may be made of silicone. However, any other suitable material may be used. It is also contemplated that fewer or more flaps may be provided, depending on the number of turns of lead 284 the user intends to wrap around header 318 and enclosure 332.

Figure 25:
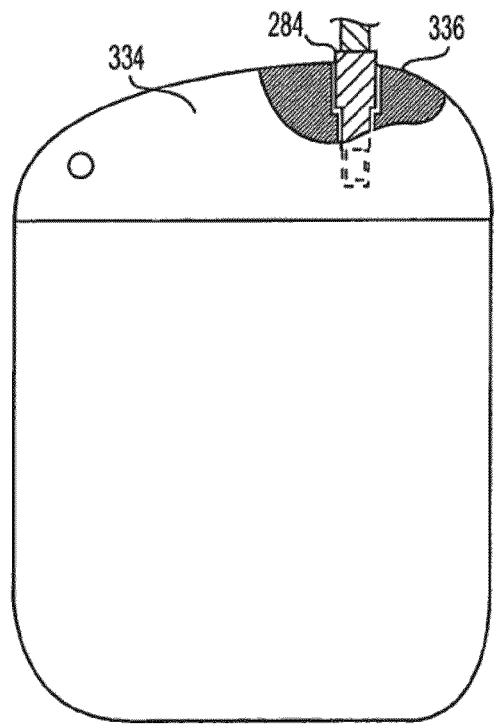
FIGS. 25-28 depict partial section views of exemplary IPGs and leads, according to further aspects of the present disclosure.

With reference now to FIG. 25, a header 334 is depicted having a bore 336 disposed in a top surface of header 334. Bore 336 that may extend along a patient's superior-inferior axis. Additionally or alternatively, bore 336 may extend in a desired direction of lead 284 when lead 284 is implanted into the patient. By realigning bore 336, it may be possible to avoid bending, and possibly damaging, lead 284.

Figure 26:
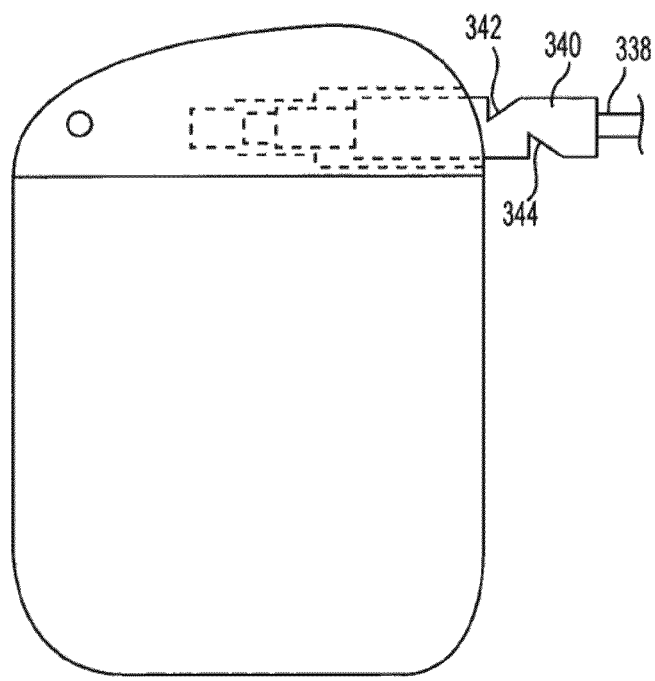

With reference now to FIG. 26, a proximal portion of lead 338 may be provided with a silicone tube or jacket 340. Jacket 340 may include one or more recesses 342 and 344. The recesses 342 and 344 may be configured to provide the user with a better grip on jacket 340. The recesses 342 and 344 may be in the form of grooves, notches, or the like. Alternatively, protrusions (not shown) may replace recesses 342 and 344 to provide a better grip. Exemplary protrusions include ridges, bumps, texturing, and/or any other suitable friction-enhancing structures.

Figure 27:
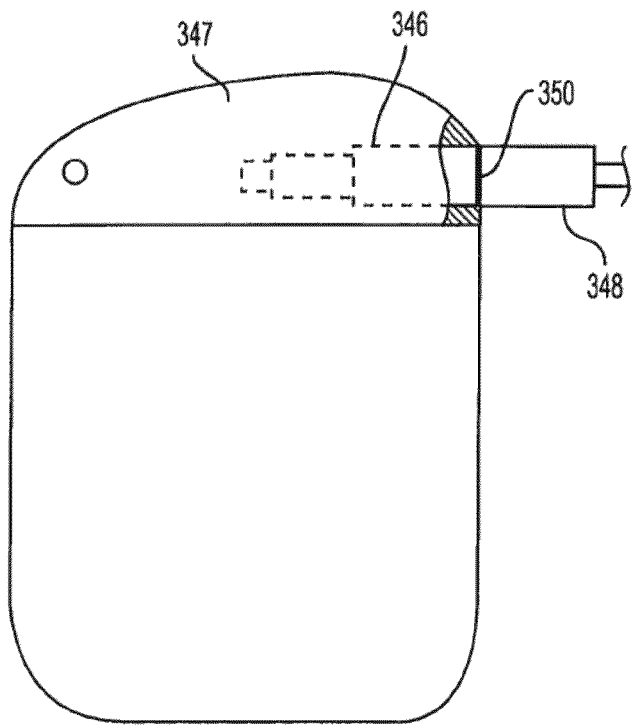

With reference to FIG. 27, bore 346 is depicted with lead 348 fully inserted into bore 346. Lead 348 may include a marker 350 on its outer surface. When lead 348 is fully inserted into bore 346, marker 350 may be aligned with a surface of header 347. This alignment may provide a visual indication to the user that full insertion has been achieved. Failure to fully insert lead 348 into bore 346 may be avoided, and/or over-insertion of lead 348 into bore 346 may be avoided. Marker 350 may include a marking applied onto the outer surface of lead 348, a recess or protrusion formed on the outer surface, a band of material, and/or any other suitable visually identifiable element.

Figure 28:
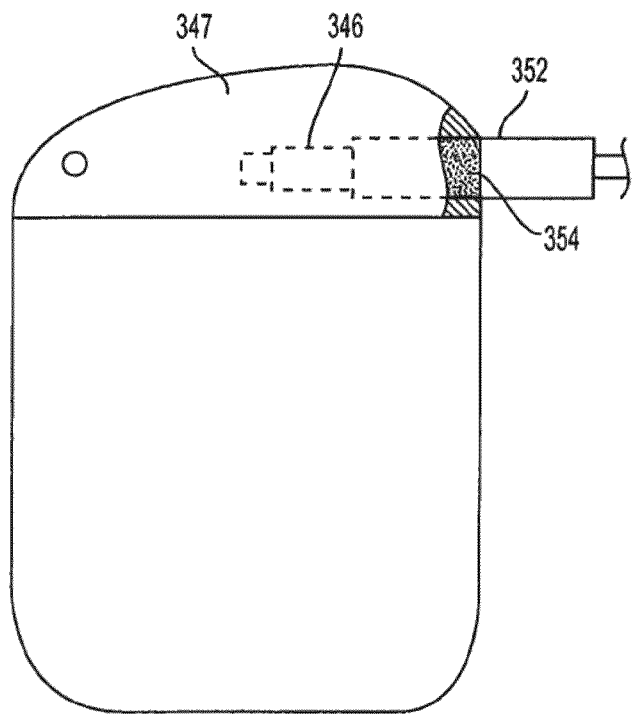

With reference now to FIG. 28, bore 346 is depicted with lead 352 fully inserted into bore 346, and lead 352 provided with a different marker 354 than marker 354. For example, marker 354 may cover an entire proximal end portion of lead 352. When lead 352 has been fully inserted into bore 346, the distal end of marker 354 may be aligned with a surface of header 347, with header 347 obscuring marker 354 and leaving none of marker 354 visible to the user. This obscuring of marker 354 may visually indicate to the user that full insertion of lead 352 has been achieved. Failure to fully insert lead 352 into bore 346 may be avoided, and/or over-insertion of lead 352 into bore 346 may be avoided. Marker 354 may include markings applied on the outer surface of the lead 352, texturing on the outer surface, a coating, and/or any other suitable visual identifiable pattern or element.

Although the aspects described above are disclosed in the context of implantable electrical stimulation systems, it should be appreciated that the principles disclosed above can be applied to other types of devices and can be implemented in different ways without departing from the scope of the disclosure as defined by the claims.

Moreover, while specific aspects may have been illustrated and described collectively herein, it should be appreciated that any subsequent arrangement designed to achieve the same or similar purpose may be substituted for the specific aspects described and shown herein. This disclosure is intended to cover any and all subsequent adaptations or variations of the various aspects. Combinations of the above aspects, and other aspects not specifically described herein, will be apparent to those of ordinary skill in the art upon reviewing the present disclosure. Further, one or more features described in one of the above-described aspects, may be used with one or more features described in any of the other above-described aspects.

Other aspects of the present disclosure will be apparent to those skilled in the art from consideration of the specification and practice of the aspects disclosed herein. It is intended that the specification and examples be considered as exemplary only, and departure in form and detail may be made without departing from the scope and spirit of the present disclosure as defined by the following claims.

What is claimed is:

1. An implantable pulse generator comprising:
    a housing having circuitry and a battery;
    a header coupled to the housing and including a bore configured to receive an end of a lead, a passage disposed transverse to the bore and extending between an exterior surface of the header and an anchor cavity that extends into the header from the bore, the header supporting at least one electrical contact within the bore coupled to the circuitry; and
    a retainer device including a looped member arranged within the bore, a proximal end extending at least partially into the passage, and anchored at a distal end by the anchor cavity, the looped member having a first position defining a first loop diameter that permits egress of the lead into the bore and having a second position defining a second loop diameter that occludes at least a portion of the bore and is configured to engage a channel recessed into the lead, the channel sufficiently engaged in the second position to prevent egress of the lead from the bore, the first loop diameter being greater than the second loop diameter.

2. The implantable pulse generator of claim 1, wherein the anchor cavity holds the retainer device at an axial position along the bore.

3. The implantable pulse generator of claim 2, wherein the retainer device is rotatable within the cavity.

4. The implantable pulse generator of claim 1, wherein the retainer device has an inner surface, the inner surface occluding at least a portion of the bore in the second position.

5. The implantable pulse generator of claim 4, wherein the inner surface of the retainer device is configured to mate with an exterior surface of the lead.

6. The implantable pulse generator of claim 5, wherein the inner surface of the retainer device is configured to be disposed in a channel on the exterior surface of the lead.

7. The implantable pulse generator of claim 1, wherein the header includes an occlusion member disposed in the passage to seal the passage from an external environment of the header.

8. The implantable pulse generator of claim 1, wherein the retainer device deflects when transitioning between the first and second positions.

9. The implantable pulse generator of claim 1, wherein the retainer device is configured to deflect when interfacing with a tool inserted through the passage.

10. The implantable pulse generator of claim 1, wherein the bore has an inner surface that defines a bore diameter, and wherein the retainer device is an arcuate member having an inner diameter in the second position, the inner diameter in the second position being less than the bore diameter.

11. The implantable pulse generator of claim 1, wherein the bore has an inner surface that defines a bore diameter, and wherein the retainer device is an elongated member disposed to abut the inner surface when in the first position and further disposed to extend across the bore when in the second position.

12. The implantable pulse generator of claim 1, wherein the bore has an inner surface that defines a bore diameter.

13. An implantable pulse generator comprising:
a housing having circuitry and a battery;
a header coupled to the housing and including a bore configured to receive an end of a lead, the header supporting at least one electrical contact within the bore coupled to the circuitry; and
a retainer device including an annular member positioned within the bore, the annular member having a first position defining a first diameter concentric with the bore and permitting egress of the lead into the bore, and a second position defining a second diameter concentric with the bore and occluding at least a portion of the bore, the annular member configured to engage the lead in the second position at an annular channel recessed into the lead, the lead engaged sufficiently to prevent egress of the lead from the bore, the first diameter being greater than the second diameter.

14. The implantable pulse generator of claim 13, wherein the header further includes a passage disposed transverse to the bore and extending between an exterior surface of the header and an anchor cavity that extends into the header from the bore, and
wherein the retainer device can be manipulated through the passage.

15. The implantable pulse generator of claim 14, wherein the header further includes an occlusion member disposed in the passage to seal the passage from an external environment of the header.

16. The implantable pulse generator of claim 14, wherein the retainer device includes a proximal end extending at least partially into the passage, and distal end anchored by the anchor cavity.

17. The implantable pulse generator of claim 13, wherein the retainer device is configured to be disposed in a channel on an exterior surface of the lead.

18. An implantable medical device comprising:
a lead having an engagement portion defining an exterior surface and an annular channel recessed into the lead from the exterior surface, the annular channel disposed between a proximal end of the exterior surface and a distal end of the exterior surface; and
an implantable pulse generator coupled to the lead and including
a housing having circuitry and a battery,
a header coupled to the housing and including a bore defining a bore axis and sized to receive the engagement portion of the lead and a passage disposed transverse to the bore axis, the header supporting at least one electrical contact within the bore coupled to the circuitry, and
a retainer device positioned within passage and not fixed to the bore, wherein the retainer device is retained within the passage to inhibited movement along the bore axis, and wherein the retainer device is moveable between a first position permitting egress of the lead into the bore, and a second position engaging the channel of the lead to inhibit egress of the lead from the bore.

19. The implantable medical device of claim 18, wherein the retainer device is moved to the second position when interfacing with a tool inserted through the passage.

20. The implantable medical device of claim 18, wherein the retainer device further includes a looped member, the looped member having a first loop diameter in the first position and a second loop diameter in the second, the looped member engages at least two opposing sides of the lead in the second position, the first loop diameter being greater than the second loop diameter.

* * * * *